(12) United States Patent
Nesterenko et al.

(10) Patent No.: US 11,643,371 B2
(45) Date of Patent: May 9, 2023

(54) ALKYL HALIDES CONVERSION INTO ETHYLENE AND PROPYLENE

(71) Applicants: TOTALENERGIES ONETECH, Courbevoie (FR); SULZER MANAGEMENT AG, Winterthur (CH)

(72) Inventors: Nikolai Nesterenko, Nivelles (BE); Gleb Veryasov, Nivelles (BE); Raoul Dethier, Schaerbeek (BE)

(73) Assignees: TOTALENERGIES ONETECH, Courbevoie (FR); SULZER MANAGEMENT AG, Winterthur (CH)

( * ) Notice: Subject to any disclaimer, the term of this patent is extended or adjusted under 35 U.S.C. 154(b) by 0 days.

(21) Appl. No.: 17/777,787

(22) PCT Filed: Nov. 20, 2020

(86) PCT No.: PCT/EP2020/082801
§ 371 (c)(1),
(2) Date: May 18, 2022

(87) PCT Pub. No.: WO2021/099526
PCT Pub. Date: May 27, 2021

(65) Prior Publication Data
US 2023/0002296 A1   Jan. 5, 2023

(30) Foreign Application Priority Data
Nov. 22, 2019 (EP) ..................................... 19315140

(51) Int. Cl.
C07C 1/26 (2006.01)
C07C 1/30 (2006.01)

(52) U.S. Cl.
CPC . *C07C 1/26* (2013.01); *C07C 1/30* (2013.01)

(58) Field of Classification Search
CPC .... C07C 1/26; C07C 1/30; B01J 29/40; B01J 29/82; B01J 29/85
See application file for complete search history.

(56) References Cited

U.S. PATENT DOCUMENTS

2008/0188701 A1   8/2008   Qi et al.
2010/0087686 A1   4/2010   Fong et al.
(Continued)

FOREIGN PATENT DOCUMENTS

CN   108187731 A   6/2018
EP   1035915 A1    9/2000
(Continued)

OTHER PUBLICATIONS

Ting Xu et al, "Fluoride-treated H-ZSM-5 as a highly selective and stable catalyst for the production of propylene from methyl halides", Journal of Catalysis., US, (Nov. 1, 2012), vol. 295, pp. 232-241.
(Continued)

*Primary Examiner* — Jafar F Parsa
(74) *Attorney, Agent, or Firm* — Ewing & Jones, PLLC

(57) ABSTRACT

The present disclosure concerns a process for converting alkyl halides to ethylene and propylene, said process comprising the steps of (a) providing a feedstream comprising alkyl halides; (b) providing a first and second catalyst composition, said second catalyst composition comprising a cracking catalyst; (c) contacting said feedstream with said first catalyst composition in a first reaction zone under first reaction conditions to provide a first product stream, and (d) subjecting at least a part of said first product stream to an Olefin Catalytic Cracking with said second catalyst composition in a second reaction zone under second reaction
(Continued)

conditions to provide a second product steam. The process is remarkable in that it further comprises a step of steaming said first catalyst composition before the step (c) and in that said first catalyst composition comprises zeolites and a binder, wherein said zeolites comprise at least one 10-membered ring channel.

20 Claims, 4 Drawing Sheets

(56) References Cited

U.S. PATENT DOCUMENTS

| | | |
|---|---|---|
| 2016/0200642 A1 | 7/2016 | Ghosh et al. |
| 2016/0347681 A1 | 12/2016 | Ghosh et al. |
| 2016/0347682 A1 | 12/2016 | Ghosh |
| 2017/0057886 A1 | 3/2017 | Fickel |

FOREIGN PATENT DOCUMENTS

| | | |
|---|---|---|
| EP | 1036136 A1 | 9/2000 |
| EP | 1036135 B1 | 9/2002 |
| EP | 1036137 B1 | 11/2002 |
| EP | 1036139 B1 | 11/2002 |
| EP | 1190015 B1 | 1/2003 |
| EP | 1036134 B1 | 4/2003 |
| EP | 1036138 B1 | 5/2003 |
| EP | 1036133 B1 | 7/2003 |
| EP | 1194500 B1 | 8/2003 |
| EP | 1363983 A1 | 11/2003 |
| EP | 1194502 B1 | 8/2006 |
| WO | 2004048299 A2 | 6/2004 |
| WO | 2016099775 A1 | 6/2016 |

OTHER PUBLICATIONS

International Search Report and Written Opinion issued in Application No. PCT/EP2020/082801 dated Feb. 11, 2021; 10 pages.
Ch. Baerlocher et al., "Atlas of Zeolite Framework Types", 6th revised edition, 2007, Elsevier.

ALKYL HALIDES CONVERSION INTO ETHYLENE AND PROPYLENE

CROSS-REFERENCE TO RELATED APPLICATIONS

This application claims the benefit of PCT/EP2020/082801 filed Nov. 20, 2020, which claims priority from EP 19315140.4 filed Nov. 22, 2019, which are incorporated herein by reference in their entireties for all purposes.

TECHNICAL FIELD

The present disclosure relates to a process for converting one or more alkyl halides selectively into ethylene and propylene.

TECHNICAL BACKGROUND

Olefins are considered to be key components of the chemical industry. Starting from alkanes, and methane in particular, it is feasible to obtain the corresponding alkyl halide, for example, methyl halide. Alkyl halide can be then transformed into olefins. By adjusting the reaction conditions and employing a specific catalyst, the ratios of these various olefins may be modified, leading to the obtaining of the desired effluents, that can be then separated by known technology. The process for converting one or more alkyl halides into olefins, namely the second step of the two-step process for producing olefins from alkanes, has already been thoroughly studied.

In US 2016/0347681, 10-membered ring-containing HZMS-5 zeolite having a silica-to-alumina ratio (SAR) comprised between 25 and 500 allows for converting methyl chloride at 350° C. with selectivity to ethylene and propylene of 38.2% and with a conversion of 35.1 after 20 hours on stream. When HZMS-5 was ion-exchanged to MgZMS-5, the conversion was increased to 99.8% but the selectivity dropped to 25.9%. A significant amount of C4 olefins was formed in both cases. In US 2016/0200642, HZMS-5 zeolite presenting a SAR of 1192 has been used. After 20 hours on stream, the selectivity to ethylene and propylene was increased to 66.7%, while the selectivity to C4 olefins reaches 21.7% and to C5+ olefins reaches 7.4%. Under these conditions, no aromatics were generated.

In US 2016/0347682, a crystalline zeolite catalyst having an STI framework topology, such as SSZ-75, was used for the conversion of an alkyl halide to olefins. In some aspects, this catalyst has shown, under reaction temperature ranging between 300° C. and 500° C., a selectivity to ethylene and propylene ranging from 70% to 90%. Besides the light olefins, the reaction produces by-products such as methane, C4-C5 olefins and BTX (benzene, toluene and xylene).

US 2008/0188701 describes the use of a silicoaluminophosphate molecular sieve catalyst, which comprises 50 wt. % of SAPO-34 molecular sieve as active component and 50 wt. % of alumina as a matrix. At a temperature of 450° C., methyl chloride, diluted with methanol in a ratio methanol/methyl chloride of 0.1:1, was converted in a fixed bed reactor with 2 grams of catalyst at 77.89% and afforded a selectivity to ethylene and propylene of 84.35% after 1 hour. Formation of C4 olefins amounts to 10.47%. However, when the reaction was conducted into a fluidized bed reactor with 75 grams of a catalyst prepared by the spray drying process, the conversion decreases to 72.78%, but the selectivity to ethylene and propylene increases to 87.59%. Formation of C4 olefins diminishes to 7.99%.

In US 2017/0057886, an aluminosilicate zeolite catalyst, i.e. a chabazite zeolite of the SSZ-13 type having relatively small pore diameter which inhibits the molecule larger than those bearing four carbon atoms to exit its framework, has been used in the olefin production from methyl halide. It is described that in particular aspects, the combined maximum selectivity of ethylene, propylene and butylene is at least 85%. The selectivity in C4 alkenes ranges between 0% and 15% and the selectivity in aromatic compounds or C2-C4 alkanes is less than 0.1%. In one instance, at a temperature of 450° C., the selectivity to ethylene and propylene was reported to be of 73.64% at a conversion of 99.65%. However, after less than 1.5 hours on stream, the catalyst gets deactivated, dropping the conversion to less than 20% after 3 hours on stream.

In WO 2016/099775, the methyl chloride transformation into olefins was studied with a SAPO zeolite catalyst. After 20 h on stream, a conversion of 34.5% was achieved and a selectivity to ethylene and propylene of 90.7% was observed. 5.0% of C4 olefins was generated.

It is admitted that any unreacted alkyl halide can be recycled and reintroduced in the alkyl halide feed to further maximize the overall conversion of alkyl halides to olefins. It is also admitted that separation steps have also to be considered for removing C4+ olefins to transform them into ethylene and propylene in additional processes. These considerations have resulted in the establishment of integrated processes to produce ethylene and propylene from alkyl halide.

In US 2010/0087686, an integrated process for producing aromatic hydrocarbons, ethylene and/or propylene from methane is described. Methane is first transformed in methyl bromide which is, in a second step, converted into higher molecular hydrocarbons. Using a coupling catalyst, for instance, zeolite with a dopant (i.e. manganese), an effluent comprising 32% of aromatics (i.e. benzene, toluene and xylenes) and thus only 68% of C2-C5 alkanes, with a minor amount of C2-C5 alkenes, methane and hydrogen bromide, is produced. The zeolite catalyst is described as being gradually deactivated by the formation of coke. Distillation steps are carried out to separate the aromatics and the C2-C5 alkanes (with also methane, hydrogen bromide and a minor concentration of C2-C5 alkenes). The aromatics are further processed to produce benzene and p-xylene, which are separated. The stream containing the C2-C5 linear alkanes (and a minor amount of C2-C5 alkenes) is first purified to remove hydrogen bromide and methane before being cracked to produce pure ethylene and pure propylene after a final separation step. Nevertheless, the important number of aromatics produced, 32%, reduces considerably the efficiency of the further treatments (numerous separation steps before and after the cracking step itself). Indeed, each of the further steps is susceptible to reduce the overall yield in ethylene and propylene.

Starting from an alkyl halide and wishing to obtain ethylene and propylene is thus not straightforward. In processes converting alkyl halide into olefins, a large amount of by-products (notably aromatics and coke) is formed, reducing thus the number of side products that need to undertake an additional step, for instance, a pre-conversion of the alkyl halide at a lower temperature to the olefinic hydrocarbons stream before the cracking step. One should also mention that this cracking step is typically performed at high temperature (>500° C.), which may lead to a partial thermal disproportionation of the alkyl halide to alkyl di-halide and $CH_4$. As a consequence, the formed alkyl di-halide transforms to heavy aromatics and may cause reactor plugging.

The facility to form alkyl halide increases in the series F<Cl<Br<I. starting from Br, the direct processing of the alky halide is practically impossible and required a pre-conversion step. However, if the alkyl halide ($CH_3Br$) is present in a mixture with olefins, the formation of coke is mitigated and the carbon from $CH_3Br$ is substantially incorporated in the olefins pool. This means that the $CH_3Br$ should be pre-converted partially or fully to hydrocarbons at low temperature or subjected to high-temperature conversion zone only in the presence of heavier hydrocarbons.

The present disclosure has thus the objective of increasing the amount of the intermediate products in a process involving at least one step of cracking for the conversion of one or more alkyl halides into ethylene and propylene.

SUMMARY

According to a first aspect, the disclosure provides a process for converting one or more alkyl halides to ethylene and propylene, said process comprising the following steps:
  a) providing a feedstream comprising one or more alkyl halides; optionally, diluted in at least one diluent;
  b) providing a first catalyst composition and a second catalyst composition, said second catalyst composition comprising a cracking catalyst;
  c) contacting said feedstream with said first catalyst composition in a first reaction zone under first reaction conditions to provide a first product stream; and
  d) subjecting at least a part of said first product stream to an Olefin Catalytic Cracking (OCC) with said second catalyst composition in a second reaction zone under second reaction conditions to provide a second product steam.

the process is remarkable in that it further comprises a step of steaming said first catalyst composition before the step (c), and in that said first catalyst composition comprises one or more zeolites and a binder, wherein said one or more zeolites comprise at least one 10-membered ring channel.

With preference, step (d) comprises subjecting said first product stream in totality, without conducting a separation step, to an Olefin Catalytic Cracking (OCC) with said second catalyst composition in a second reaction zone under second reaction conditions to provide a second product steam.

The first and second catalyst compositions can be the same or different.

Surprisingly, it has been found that both a high selectivity to acyclic C3-C6 olefins and a high conversion can be achieved with the use of a first catalyst composition wherein at least one zeolite has a structure shaped with a binder. The presence of the binder, preferentially a silica binder, allows for enhancing the selectivity toward acyclic C3-C6 olefins while keeping at the same time the selectivity to ethylene and aromatics low, which has for effect that these acyclic C3-C6 olefins can be used as intermediate products in the process for converting one or more alkyl halides to ethylene and propylene in which these intermediate products are transformed into ethylene and propylene under cracking conditions. Indeed, as demonstrated in the examples, a selectivity of at least 70% for the acyclic C3-C6 olefins can be achieved together with a conversion rate of the one or more alkyl halides of at least 20%. In addition, as demonstrated in the examples, a selectivity of at least 75% for the acyclic C3-C6 olefins can be achieved together with selectivity to ethylene of less than 5%, preferably less than 1% and with selectivity to aromatics of less than 15%, preferably less than 11%.

In a preferred embodiment, said one or more zeolites of the first catalyst composition contain less than 1000 wt. ppm of alkali metals as determined by XRF based on the total weight of the one or more zeolites and/or less than 5000 wt. ppm of transition metals as determined by XRF based on the total weight of the one or more zeolites. The content of the alkali metals is below 5000 wt. ppm as determined by XRF based on the total weight of the one or more zeolites, preferably below 2500 wt. ppm. The content of the alkaline earth metals is below 5000 wt. ppm as determined by XRF based on the total weight of the one or more zeolites, preferably below 2500 wt. ppm. However, the first catalyst composition may contain a higher amount of alkaline earth metals as a component of the binder (e.g. $Ca_3(PO_4)_2$). So, additional traces of these metals may be present on the catalyst as impurities from the binder.

In a preferred embodiment, one or more zeolites of the catalyst composition are free of metal other than aluminium.

For example, said one or more zeolites of the catalyst composition are free of gallium and/or cerium and/or zinc. In a more general way, the one or more zeolites of the catalyst composition are free of transition metals, and/or are free of rare earth elements, and/or are free of lanthanides, and/or are free of alkaline earth metals, and/or are free of alkali metals.

In a preferred embodiment, said one or more zeolites contain less than 1000 wt. ppm of alkali metals as determined by XRF based on the total weight of the one or more zeolites and/or less than 2500 wt. ppm of transition metals based on the total weight of the one or more zeolites.

For example, said one or more zeolites of the catalyst composition contain less than 5000 wt. ppm of alkali metals as determined by XRF based on the total weight of the one or more zeolites before the step of steaming; preferably, below 2500 wt. ppm, more preferably below 1000 wt. ppm.

For example, said one or more zeolites of the catalyst composition contains less than 5000 wt. ppm of alkaline earth metals as determined by XRF based on the total weight of the one or more zeolites before the step of steaming; preferably, below 2500 wt. ppm; more preferably, below 1000 wt. ppm. However, the final catalyst composition may contain a higher amount of alkaline earth metals as a component of the binder (e.g. $Ca_3(PO_4)_2$). So, additional traces of these metals may be present on the catalyst as impurities from the binder.

For example, said one or more zeolites of the catalyst composition contains less than 5000 wt. ppm of lanthanides as determined by XRF based on the total weight of the one or more zeolites before the step of steaming; preferably, below 2500 wt. ppm; more preferably, below 1000 wt. ppm.

For example, said one or more zeolites of the catalyst composition contains less than 5000 wt. ppm of rare earth elements as determined by XRF based on the total weight of the one or more zeolites before the step of steaming; preferably, below 2500 wt. ppm; more preferably, below 1000 wt. ppm.

With preference, one or more of the following embodiments can be used to better define the first catalyst composition used in the process:
  The one or more zeolites have a crystal size below 2000 nm, as determined by scanning electron microscopy (SEM), preferentially below 1750 nm, more preferentially below 1500 nm, even more preferentially below 1250 nm or below 1000 nm.
  The one or more zeolites have a crystal size of at least 10 nm as determined by scanning electron microscopy (SEM), for example of at least 50 nm, or at least 100 nm, or at least 200 nm, or at least 400 nm or at least 600 nm.

The one or more zeolites comprising at least one 10-membered ring channel, with crystal size below 2000 nm, have a Si/Al molar ratio in the framework of the zeolite ranging from 10 to 1500 as determined by TPD after the step of steaming; preferably ranging from 80 to 1200; more preferably ranging from 150 to 1100 and most preferably from 800 to 1000.

The one or more zeolites have a Si/Al molar ratio in the framework of the zeolite of at least 10 as determined by TPD before the step of steaming; and/or a Si/Al molar ratio in the framework of the zeolite of at least 80 as determined by TPD after the step of steaming; with preference, of at least 150.

The one or more zeolites have a Si/Al molar ratio in the framework of the zeolite ranging from 80 to 1500 as determined by TPD after the step of steaming; preferably ranging from 150 to 1200; more preferably ranging from 400 to 1100 and most preferably from 800 to 1000.

The one or more zeolites are dealuminated with an organic acid solution or with an inorganic solution.

The one or more zeolites in the first catalyst composition are selected from the group of MFI, MEL, FER, MTT, MWW, TON, EUO and MRE families.

The one or more zeolites in the first catalyst composition are selected from the group of MFI, MEL, FER, MTT, MWW, TON, EUO and MRE families, said one or more zeolites having a Si/Al molar ratio in the framework of the zeolite of at least 10 as determined by TPD before the step of steaming; and/or a Si/Al molar ratio in the framework of the zeolite of at least 80 as determined by TPD after the step of steaming; with preference, of at least 150.

The one or more zeolites are selected from the MFI family.

The one or more zeolites are or comprise zeolites from the MFI family; with preference, with a Si/Al molar ratio in the framework of the zeolite of at least 10 as determined by TPD.

The one or more zeolites are or comprise zeolites from the MFI family wherein said one or more zeolites are MFI zeolites with a Si/Al molar ratio in the framework of the zeolite of at least 10 as determined by TPD before the step of steaming and/or are MFI zeolites with a Si/Al molar ratio in the framework of the zeolite of at least 80 as determined by TPD after the step of steaming.

The one or more zeolites are zeolites selected from the silicalites from the MFI family and/or silicalites from the MEL family having a Si/Al molar ratio in the framework of the zeolite of at least 10 as determined by TPD before the step of steaming; and/or a Si/Al molar ratio in the framework of the zeolite of at least 80 as determined by TPD after the step of steaming; with preference of at least 150.

The one or more zeolites are selected from the list comprising ZSM-5, silicalites from the MFI family, boralite C, TS-1, ZSM-11, silicalites from the MEL family, boralite D, TS-2, SSZ-46, ferrierite, FU-9, ZSM-35, ZSM-23, MCM-22, PSH-3, ITQ-1, MCM-49, ZSM-22, Theta-1, NU-10, ZSM-50, EU-1 and ZSM-48, said one or more zeolites having a Si/Al molar ratio in the framework of the zeolite of at least 10 as determined by TPD before the step of steaming; and/or a Si/Al molar ratio in the framework of the zeolite of at least 80 as determined by TPD after the step of steaming; with preference, of at least 150.

The one or more zeolites in the first catalyst composition are or comprise MFI zeolites having a Si/Al molar ratio in the framework of the zeolite of at least 10 as determined by TPD and are subjected to a step of steaming before step (c) followed by modification with phosphorous; with preference, the one or more zeolites are ZSM-5.

The one or more zeolites in the first catalyst composition are modified with phosphorus.

At least 50 wt. % of said one or more zeolites are in their hydrogen form as based on the total weight of the zeolites.

The first catalyst composition comprises at least 60 wt. % of one or more zeolites comprising at least one acid 10-membered ring channel, preferably at least 70 wt. %, more preferably at least 80 wt. %, even more preferably at least 90 wt. % and most preferably 100 wt. %.

The one or more zeolites have weak Brønsted acid sites in a concentration inferior to 40 μmol/g-cat and strong Brønsted acid sites in a concentration superior to 40 μmol/g-cat as determined by $NH_3$—Temperature Programmed Desorption.

The one or more zeolites have Brønsted acid sites in a concentration inferior to 100 μmol/g-cat as determined by $NH_3$—Temperature Programmed Desorption, preferentially inferior to 90 μmol/g-cat, more preferentially inferior to 80 μmol/g-cat.

The first catalyst composition further comprises at least 0.1 wt. % of phosphorous based on the total weight of the first catalyst composition, preferentially with at least 0.5 wt. % of phosphorous, more preferentially with at least 1.0 wt. % of phosphorous, even more preferentially with at least 1.5 wt. % of phosphorous. In a preferred embodiment, the first catalyst composition is modified with 2.3 wt. % of phosphorous.

The first catalyst composition is modified with phosphoric acid; and/or the first catalyst composition comprises phosphoric acid and magnesium nitrate.

The first catalyst composition modified with phosphorous is blended with at least one metal-containing material; with preference, the at least one metal-containing material is one or more selected from an alkaline earth metal-containing material; magnesium nitrate; and a cerium-containing material.

The first catalyst composition is blended with at least one metal-containing material; with preference, the at least one metal-containing material is an alkaline earth metal-containing material which comprises at least one alkaline earth metal is selected from beryllium, magnesium, calcium, strontium, barium and any mixtures thereof, and/or the at least one metal-containing material has an anion selected from the group of oxides, silicates, aluminates, titanates, phosphates, borates and borosilicates.

The one or more zeolites are doped with a phosphorus-containing material before or after the steaming step, to form one or more phosphate zeolites.

The one or more zeolites are one or more phosphate zeolites and are further subjected to a steaming step.

The first catalyst composition comprises between 0.1 wt. % and 7.0 wt. % of a phosphorus-containing material as based on the total weight of the first catalyst composition, preferably between 0.3 wt. % and 4.5 wt. %, preferentially between 0.5 wt. % and 4.0 wt. %, more preferentially 2.0 wt. %.

The one or more zeolites are doped with at least one phosphorus-containing material and with at least one alkaline earth metal-containing material, preferably at least one alkaline earth metal-containing material is selected from at least one magnesium-containing material and/or at least one calcium-containing material.

The binder is selected from silica, clays, calcium phosphates, magnesium phosphates, and mullite. Most preferentially, the binder is silica.

The binder is free of aluminium compounds; i.e. the binder does not contain aluminium compounds, such as alumina.

The binder is present in an amount of at least 10 wt. % as based on the total weight of the first catalyst composition; preferably in an amount of at least 20 wt. %, most preferably in an amount of 30 wt. %, even more preferably in an amount of at least 40 wt. %, and most preferably in an amount of at least 50 wt. %.

In a preferred embodiment, the first catalyst composition is calcinated before said step (c) of contacting the feedstream; with preference, the first catalyst composition is calcined at a temperature of at least 400° C.

With preference, one or more of the following embodiments can be used to better define the second catalyst composition used in the process:

Said cracking catalyst comprises one or more zeolites and/or one or more clays; with preference, said cracking catalyst comprises one or more zeolites selected from silicalites from the MFI family, crystalline silicate from the MFI family with a Si/Al atomic ratio of at least 180, crystalline silicate from the MEL family with a Si/Al atomic ratio ranging between 150 and 800, and/or phosphorous-modified zeolite from the MFI, MEL, FER, or MOR family. More preferably, said cracking catalyst comprises one or more zeolites selected from silicalites from the MFI family, optionally with a silica binder.

Said cracking catalyst comprises one or more zeolites with a binder; preferably, a silica binder.

Said cracking catalyst can be subjected to a steaming step before step (d).

The process can be carried out in one or more fixed bed reactors and/or in one or more fluidized bed reactors.

In an embodiment wherein the process is carried out in one reactor, said reactor comprises at least a first reaction zone and a second reaction zone, the second reaction zone being downstream of the first reaction zone, and the first catalyst composition is provided into the first reaction zone and the second catalyst composition is provided into the second reaction zone.

In an embodiment wherein the process is carried out in one reactor comprising at least two vessels, the first catalyst composition is provided into the first vessel of one reactor forming a first reaction zone, and the second catalyst composition is provided in the second vessel of said one reactor forming a second reaction zone, said second vessel being downstream of said first vessel.

In an embodiment wherein the process is carried out in at least two reactors, the first catalyst composition is provided into a first reactor forming a first reaction zone, and the second catalyst composition is provided into a second reactor forming a second reaction zone, the second reactor being downstream of the first reactor and fluidly connected to the first reactor.

With preference, one or more of the following embodiments can be used to better define the step (a) of the process:

The one or more alkyl halides in the feedstream of step (a) comprise one or more monohalo-alkyl, preferably methyl bromide.

The one or more alkyl halides in the feedstream of step (a) comprise one or more monohalo-akly with at most 10 wt. % of polyhalo-alkyl, such as dihalo-alkyl, trihalo-alkyl and/or tetrahalo-alkyl.

The one or more alkyl halides in the feedstream of step (a) comprise a mixture of one or more selected from monohalo-alkyl, dihalo-alkyl, trihalo-alkyl and/or tetrahalo-alkyl; with preference, the mixture comprises the monohalo-alkyl in an amount of at least 90 wt. % of said mixture.

The alkyl of said one or more alkyl halides is methane, ethane, propane and/or any mixture thereof.

The halogen of said one or more alkyl halides is selected from fluorine, chlorine, bromine, iodine and/or any mixture thereof.

The one or more alkyl halides are substantially free of oxygenates, with preference free of methyl, ethyl and/or propyl.

The one or more alkyl halides are diluted with an inert oxygenated compound, such as $CO_2$.

The one or more alkyl halides are diluted into $N_2$, hydrogen halides, $H_2$, $CO_2$, non-converted $CH_4$, $CO$, $C_2H_6$, $C_3H_8$, and/or $C_4H_{10}$, more preferably gaseous nitrogen.

With preference, one or more of the following embodiments can be used to better define the step of steaming of the process:

The one or more steamed zeolites of the first catalyst composition are leached with an organic or inorganic acid solution, before the step (c). The steaming and the leaching of the first catalyst composition are performed subsequently, the steaming step being conducted first.

Said step of steaming is carried out at a temperature ranging between 300° C. and 800° C., preferentially ranging between 400° C. and 750° C.

Said step of steaming is carried out at a partial pressure of the steam ranging between 0.01 kPa and 20 kPa, preferentially between 0.5 kPa and 1.5 kPa.

Said step of steaming is followed by an extraction step, with preference with a monoprotic acid selected from HCl, $HNO_3$, HBr, acetic acid or formic acid.

Said step of steaming is followed by an extraction step, with preference with a complexing agent or with an aqueous complexing agent.

Said step of steaming is followed by an extraction step and by a calcination step; with preference, said calcination step is carried out in a steam-free atmosphere at a temperature ranging between 550° C. and 700° C., preferentially at a temperature ranging between 600° C. and 650° C.

Said step of steaming is followed by a calcination step; with preference, said calcination step is carried out in a steam-free atmosphere at a temperature ranging between 550° C. and 700° C., preferentially at a temperature ranging between 600° C. and 650° C.

Said step of steaming is followed by a step of modification of the steamed catalyst by phosphorous.

In an embodiment, said step of steaming is followed by a step of modification of the steamed catalyst by phosphorous under reduced or atmospheric pressure, preferentially at a temperature from 10 to 400° C., more preferentially at a temperature from 50° C. to 350° C., even more preferentially at a temperature from 100° C. to 300° C. With preference:
- The source of phosphorous in the modification step of the steamed catalyst is mixed in an aqueous or a non-aqueous medium.
- The source of phosphorous in the modification step of the steamed catalyst is mixed in a non-aqueous medium selected from the group of ethanol, methanol and/or other alcohols.
- The source of phosphorous is phosphoric acid, preferably a solution of phosphoric acid.
- The modification step of the steamed catalyst is followed by a calcination step; with preference, said calcination step is carried out in a steam-free atmosphere at a temperature ranging between 550° C. and 700° C., preferentially at a temperature ranging between 600° C. and 650° C.
- The modification step of the steamed catalyst is followed by a further step of steaming, preferentially at a steam partial pressure comprised between 0.1 and 1.0 kPa and/or at a temperature comprised between 550 and 750° C. and/or for a period of from 0.5 to 10 hours.
- The modification step of the steamed catalyst is followed by a calcination step and by a further step of steaming, preferentially at a steam partial pressure comprised between 0.1 and 1.0 kPa and/or at a temperature comprised between 550 and 750° C. and/or for a period of from 0.5 to 10 hours.

With preference, one or more of the following embodiments can be used to better define the step (c) of the process:
- Step (c) has a conversion rate of at least 20% of the one or more alkyl halides into hydrocarbons; with preference, of at least 30%.
- The reaction conditions of step (c) include a reaction temperature ranging from 150° C. to 380° C., preferably ranging from 250° C. to 350° C.; more preferably ranging from 260° C. to 340° C.; even more preferably ranging from 280° C. to 320° C., most preferably at a temperature of 300° C.
- The reaction conditions of step (c) include a weight hourly space velocity of said one or more alkyl halides comprised between 0.1 $h^{-1}$ and 100 $h^{-1}$, preferably comprised between 1.0 $h^{-1}$ and 15 $h^{-1}$, more preferably comprised between 1.5 $h^{-1}$ and 10 $h^{-1}$, even more preferably comprised between 2.0 $h^{-1}$ and 6.0 $h^{-1}$.
- The reaction conditions of step (c) include a partial pressure of said one or more alkyl halides ranging from 10 kPa to 500 kPa, preferably ranging from 20 kPa to 300 kPa, more preferably ranging from 50 kPa to 200 kPa.

With preference, one or more of the following embodiments can be used to better define the step (d) of the process:
- The second reaction conditions of step (d) include a reaction temperature ranging from 500° C. to 600° C.; preferably ranging from 510° C. to 590° C., more preferably ranging from 520° C. to 580° C.
- The second reaction conditions of step (d) include a weight hourly space velocity comprised between 0.1 $h^{-1}$ and 100 $h^{-1}$, preferably comprised between 1 $h^{-1}$ and 15 $h^{-1}$, more preferably comprised between 1.5 $h^{-1}$ and 10 $h^{-1}$, even more preferably comprised between 2.0 $h^{-1}$ and 6.0 $h^{-1}$.
- The second reaction conditions of step (d) include a pressure ranging from 0.1 MPa to 2 MPa, preferably ranging from 0.2 to 1 MPa.

In one embodiment, the step (d) of contacting said first product stream with said second catalyst composition is followed by a step (e) of performing a separation of ethylene and propylene from the said second product stream. With preference, said separation further comprises separating from the second product stream a C4+ stream, and, optionally, an additional step of separating C8+ hydrocarbons and C4-C7 compounds from said C4+ stream is carried out, said C4-C7 compounds being preferentially recycled to the second reaction zone.

In one preferred embodiment, step (c) further comprises separating from the first product stream a C4+ stream and the step (d) comprises subjecting said C4+ stream to an Olefin Catalytic Cracking (OCC) with said second catalyst composition in a second reaction zone under second reaction conditions to provide a second product stream, said step (d) being optionally followed by a step (e) of performing a separation of ethylene and propylene from said second product stream, said step (e) preferentially comprising the following sub-steps:
  i. separating C8+ hydrocarbons from the said second product stream, to provide a C8+ hydrocarbons stream and a remaining stream from said second product stream;
  ii. performing a separation of ethylene and propylene from the remaining stream of the said second product stream.

In one preferred embodiment, the step (c) further comprises separating from the first product stream a C4+ stream and separating from said C4+ stream a high boiling point fraction and a low boiling point fraction; and the step (d) comprises subjecting said low boiling point fraction to an Olefin Catalytic Cracking (OCC) with said second catalyst composition in a second reaction zone under second reaction conditions to provide a second product stream, said step (d) being optionally followed by a step (e) of performing a separation of ethylene and propylene from said second product stream, said step (e) preferentially comprising the following sub-steps:
  i. separating from said second product stream the C4+ compounds, to provide a C4+ stream and a remaining stream from said second product stream;
  ii. performing a separation of ethylene and propylene from the remaining stream of the said second product stream.

In an embodiment, the step (d) further comprises reinjecting at least a part of said first product stream or of said a C4+ stream into the feedstream of step (a).

In an embodiment, step (c) further comprises separating from the first product stream in a C2=/C2 stream; with preference, the step (d) further comprises reinjecting at least a part of said C2=/C2 stream into the feedstream of step (a).

In an embodiment, said process further comprises one or more of the following sub-steps:
  i. removing hydrogen halide from said first product stream before the step (d) or from said second product stream after the step (d);
  ii. recovering at least a part of the unreacted one or more alkyl halides before or after the step (d), preferentially followed by a step of reinjecting said at least a part of unreacted one or more alkyl halides into the feedstream of step (a);
  iii. removing aromatics from said first product stream before the step (d) or from said second product stream after the step (d).

According to a second aspect, the disclosure provides the use of a catalyst composition in a process for converting alkyl halide to ethylene and propylene according to the first aspect, wherein said catalyst composition is a first catalyst composition, remarkable in that said first catalyst composition comprises one or more zeolites and a binder, wherein said one or more zeolites comprise at least one 10-membered ring channel, and further wherein said first catalyst composition is steamed before use.

DETAILED DESCRIPTION

Figure 1:
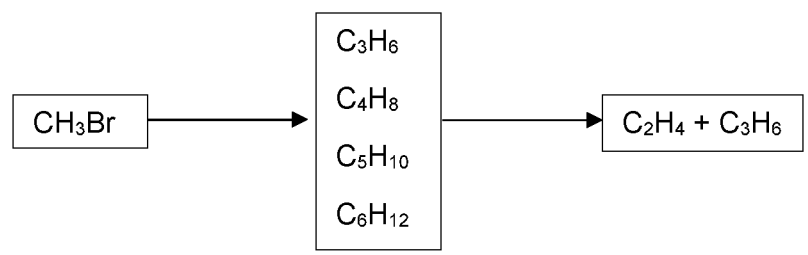
FIG. 1 schematically illustrates the process of the present disclosure.

For the disclosure, the following definitions are given: Zeolite codes (e.g., CHA . . . ) are defined according to the "*Atlas of Zeolite Framework Types*", 6$^{th}$ revised edition, 2007, Elsevier, to which the present application also refers.

The terms "alkane" or "alkanes" as used herein describe acyclic branched or unbranched hydrocarbons having the general formula $C_nH_{2n+2}$, and therefore consisting entirely of hydrogen atoms and saturated carbon atoms; see e.g. IUPAC. Compendium of Chemical Terminology, 2nd ed. (1997). The term "alkanes" accordingly describes unbranched alkanes ("normal-paraffins" or "n-paraffins" or "n-alkanes") and branched alkanes ("iso-paraffins" or "iso-alkanes") but excludes naphthenes (cycloalkanes).

The term "aromatic hydrocarbons" or "aromatics" relates to cyclically conjugated hydrocarbon with a stability (due to derealization) that is significantly greater than that of a hypothetical localized structure (e.g. Kekule structure). The most common method for determining aromaticity of a given hydrocarbon is the observation of diatropicity in the $^1$H NMR spectrum.

The terms "olefin" or "alkene" as used herein relate to an unsaturated hydrocarbon compound containing at least one carbon-carbon double bond.

The terms "mono-olefin" as used herein relates to an unsaturated hydrocarbon compound containing one single carbon-carbon double bond.

The SAR of one or more zeolites refers to the silica to alumina molar ratio of said one or more zeolites. SAR is determined by $NH_3$—Temperature Programmed Desorption.

As used herein, the term "C# hydrocarbons", wherein "#" is a positive integer, is meant to describe all hydrocarbons having # carbon atoms. C# hydrocarbons are sometimes indicated as just C#. Moreover, the term "C#+ hydrocarbons" is meant to describe all hydrocarbon molecules having # or more carbon atoms. Accordingly, the expression "C5+ hydrocarbons" is meant to describe a mixture of hydrocarbons having 5 or more carbon atoms.

The symbol "=" in the term "C#=hydrocarbon" indicates that the hydrocarbon concerned is an olefin or an alkene, the notation "=" symbolizing the carbon-carbon double bond. For instance, "C6=" stands for "C6 olefin", or for olefin comprising 6 carbon atoms.

The term "steam" is used to refer to water in the gas phase, which is formed when water boils.

The term "alkali metal" refers to an element classified as an element from group 1 of the periodic table of elements (or group IA), excluding hydrogen. According to this definition, the alkali metals are Li, Na, K, Rb, Cs and Fr.

The term "alkaline earth metal" refers to an element classified as an element from group 2 of the periodic table of elements (or group IIA). According to this definition, the alkaline earth metals are Be, Mg, Ca, Sr, Ba and Ra.

The term "transition metal" refers to an element whose atom has a partially filled d sub-shell, or which can give rise to cations with an incomplete d sub-shell (IUPAC definition). According to this definition, the transition metals are Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg, Ac, Rf, db, Sg, Bh, Hs, Mt, Ds, Rg, and Cn. The term "transition metal" includes the group 12 elements i.e. Zn, Cd and Hg.

The term "rare earth elements" refers to the fifteen lanthanides, as well as scandium and yttrium. The 17 rare-earth elements are cerium (Ce), dysprosium (Dy), erbium (Er), europium (Eu), gadolinium (Gd), holmium (Ho), lanthanum (La), lutetium (Lu), neodymium (Nd), praseodymium (Pr), promethium (Pm), samarium (Sm), scandium (Sc), terbium (Tb), thulium (Tm), ytterbium (Yb), and yttrium (Y).

The term "lanthanides" corresponds to the 15 metallic chemical elements with atomic numbers 57-71, from lanthanum through lutetium.

The yield to particular chemical compounds is determined as the mathematical product between the selectivity to said particular chemical compounds and the conversion rate of the chemical reaction. The mathematical product is expressed as a percentage.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all integer numbers and, where appropriate, fractions subsumed within that range (e.g. 1 to 5 can include 1, 2, 3, 4, 5 when referring to, for example, a number of elements, and can also include 1.5, 2, 2.75 and 3.80, when referring to, for example, measurements). The recitation of endpoints also includes the recited endpoint values themselves (e.g. from 1.0 to 5.0 includes both 1.0 and 5.0). Any numerical range recited herein is intended to include all sub-ranges subsumed therein.

The particular features, structures, characteristics or embodiments may be combined in any suitable manner, as would be apparent to a person skilled in the art from this disclosure, in one or more embodiments.

The disclosure provides a process for converting one or more alkyl halides to ethylene and propylene, said process comprising the following steps:
  a) providing a feedstream comprising one or more alkyl halides; optionally, diluted in at least one diluent;
  b) providing a first catalyst composition and a second catalyst composition, said second catalyst composition comprising a cracking catalyst;

c) contacting said feedstream with said first catalyst composition in a first reaction zone under first reaction conditions to provide a first product stream; and d) subjecting at least a part of said first product stream to an Olefin Catalytic Cracking (OCC) with said second catalyst composition in a second reaction zone under second reaction conditions to provide a second product steam;

according to the disclosure, said process further comprises a step of steaming said first catalyst composition before the step (c) and said first catalyst composition comprises one or more zeolites and a binder, wherein said one or more zeolites comprise at least one 10-membered ring channel.

The two chemical reactions involved in the process according to the disclosure are schematically represented in FIG. 1.

The First Catalyst Composition

It is preferred that the one or more zeolites, namely the one or more zeolites before the step of steaming, or the non-steamed one or more zeolites, do not contain any alkali metals since these metals may significantly reduce catalyst activity and neutralize acid sites. In a preferred embodiment, said one or more zeolites have an initial content of less than 1000 wt. ppm of alkali metals as determined by XRF as based on the total weight of the one or more zeolites.

It is preferred that the one or more zeolites, namely the one or more zeolites before the step of steaming, do not contain any alkaline earth metal since these metals may impact the steam dealumination process and retain halogen after the reaction. The retained halogen will be released during the regeneration and irreversibly deactivate zeolites.

In the case where the one or more zeolites are doped with at least one phosphorus-containing material and at least one alkaline earth metal-containing material, the alkaline earth metal is strongly bound with the phosphorous and is less prone to the formation of halides.

In a preferred embodiment, said one or more zeolites, before the steaming step, contain less than 5000 wt. ppm of alkaline earth metals as determined by XRF as based on the total weight of the one or more zeolites.

It is preferred that the first catalyst composition does not contain any transition metal since this leads to a completely distinct reactivity resulting in coke formation. This is why the first catalyst composition is devoid of any transition metal. This means that the content of the transition metals is below 5000 wt. ppm as determined by XRF in the one or more zeolites, preferably below 2500 wt. ppm in the one or more zeolites. Traces of these metals may be present on the catalyst as impurities from the binder.

For example, said one or more zeolites of the catalyst composition are free of gallium and/or cerium. For example, said one or more zeolites of the catalyst composition are free of zinc. In a more general way, the one or more zeolites of the catalyst composition are free of transition metals, and/or are free of rare earth elements, and/or are free of lanthanides, and/or are free of alkaline earth metals, and/or are free of alkali metals.

In a preferred embodiment, said one or more zeolites contain less than 1000 wt. ppm of alkali metals as determined by XRF based on the total weight of the one or more zeolites and/or less than 2500 wt. ppm of transition metals based on the total weight of the one or more zeolites.

For example, said one or more zeolites of the catalyst composition contain less than 5000 wt. ppm of alkali metals as determined by XRF based on the total weight of the one or more zeolites before the step of steaming; preferably, below 2500 wt. ppm, more preferably below 1000 wt. ppm.

For example, said one or more zeolites of the catalyst composition contains less than 5000 wt. ppm of alkaline earth metals as determined by XRF based on the total weight of the one or more zeolites before the step of steaming; preferably, below 2500 wt. ppm; more preferably, below 1000 wt. ppm. However, the final catalyst composition may contain a higher amount of alkaline earth metals as a component of the binder (e.g. $Ca_3(PO_4)_2$). So, additional traces of these metals may be present on the catalyst as impurities from the binder.

For example, said one or more zeolites of the catalyst composition contains less than 5000 wt. ppm of lanthanides as determined by XRF based on the total weight of the one or more zeolites before the step of steaming; preferably, below 2500 wt. ppm; more preferably, below 1000 wt. ppm.

For example, said one or more zeolites of the catalyst composition contains less than 5000 wt. ppm of rare earth elements as determined by XRF based on the total weight of the one or more zeolites before the step of steaming; preferably, below 2500 wt. ppm; more preferably, below 1000 wt. ppm.

The one or more zeolites comprise at least one acid 10-membered ring channel; with preference, the one or more zeolites are one or more selected from the list comprising MFI, MEL, FER, MTT, MWW, TON, EUO and MRE families, preferentially from the MFI family and/or the MEL family. These zeolites or molecular sieves are aluminosilicate catalysts that have a chemical structure that is largely different from the chemical structure of the aluminophosphate and silicoaluminophosphate molecular sieves.

With preference, the zeolite from the MFI family is selected from ZSM-5, silicalites, boralite C, or TS-1. Preferentially, the zeolites are silicalites from the MFI family or ZSM-5, more preferentially the zeolites are silicalites from the MFI family. The zeolites from the MEL family are, preferentially, selected from ZSM-1, silicalites, boralite D, TS-2, or SSZ-46. Preferentially, the zeolites are silicalites from the MEL family. The zeolites from the FER family are, preferentially, selected from ferrierite, FU-9 or ZSM-35. The zeolites from the MTT family are, preferentially, ZSM-23. The zeolites from the MWW family are, preferentially, selected from MCM-22, PSH-3, ITQ-1, or MCM-49. The zeolites from the TON family are, preferentially, selected from ZSM-22, Theta-1, or NU-10. The zeolites from the EUO family are, preferentially, selected from ZSM-50 or EU-1. The zeolites from the MRE family are, preferentially, ZSM-48.

Therefore, in a preferred embodiment, the first catalyst composition comprises one or more zeolites with at least one acid 10-membered ring channel.

Advantageously, the one or more zeolites have a crystal size below 2000 nm as determined by scanning electron microscopy (SEM), preferentially below 1750 nm, more preferentially below 1500 nm and even more preferentially below 1250 nm or below 1000 nm. The fact that one or more zeolites have a small size allows for better accessibility of the reactants to the catalyst, which renders the catalyst more active.

Advantageously, the one or more zeolites have a crystal size of at least 10 nm as determined by scanning electron microscopy (SEM), for example of at least 50 nm, or at least 100 nm, or at least 200 nm, or at least 400 nm or at least 600 nm.

For example, the one or more zeolites have an average crystal size ranging from 10 nm to below 2000 nm as determined by scanning electron microscopy (SEM); for example, ranging from 50 nm to below 1750 nm; for example, ranging from 100 nm to below 1500 nm; and for example, ranging from 200 nm to below 1250 nm; for example, ranging from 400 nm below 1000 nm; for example, ranging from 600 nm to below 800 nm.

The first catalyst composition comprising one or more zeolites is steamed before the step (c) of contacting said feedstream with the said first catalyst composition under reaction conditions to obtain a higher Si/Al molar ratio relative to the non-steamed one or more zeolites.

Advantageously, the one or more zeolites are selected from the list comprising ZSM-5, silicalites from the MFI family, boralite C, TS-1, ZSM-11, silicalites from the MEL family, boralite D, TS-2, SSZ-46, ferrierite, FU-9, ZSM-35, ZSM-23, MCM-22, PSH-3, ITQ-1, MCM-49, ZSM-22, Theta-1, NU-10, ZSM-50, EU-1 and ZSM-48, said one or more zeolites having a Si/Al molar ratio in the framework of the zeolite of at least 10 as determined by TPD before the step of steaming.

Advantageously, the one or more zeolites are selected from the list comprising ZSM-5, silicalites from the MFI family, boralite C, TS-1, ZSM-11, silicalites from the MEL family, boralite D, TS-2, SSZ-46, ferrierite, FU-9, ZSM-35, ZSM-23, MCM-22, PSH-3, ITQ-1, MCM-49, ZSM-22, Theta-1, NU-10, ZSM-50, EU-1 and ZSM-48, said one or more zeolites having a Si/Al molar ratio in the framework of the zeolite of at least 80 as determined by TPD after the step of steaming, with preference, of at least 150.

In a preferred embodiment, the first catalyst composition comprises 3D zeolites without cages (cavities) and containing at least one acid 10-membered ring channel.

Preferably, the catalyst composition comprises at least 60 wt. % of one or more zeolites having at least one acid 10-membered ring channel, more preferably at least 70 wt. %, even more preferably at least 80 wt. % and most preferably at least 90 wt. % or 95 wt. %, or 100 wt. %.

To provide an appropriate acidity, it is preferred that the zeolites are at least partly in their hydrogen form or at least partly in their ammonia form. Preferably more than 50 wt. % of the total amount of the zeolites used are in their hydrogen form or their ammonia form, preferably at least 80 wt. %, more preferably at least 90 wt. %, and even more preferably 100 wt. % of the zeolites are in their hydrogen form or their ammonia form.

The one or more zeolites have weak Brønsted acid sites in a concentration inferior to 40 μmol/g-cat and strong Brønsted acid sites in a concentration superior to 40 μmol/g-cat as determined by $NH_3$-TPD. The one or more zeolites have Brønsted acid sites in a concentration inferior to 100 μmol/g-cat as determined by $NH_3$-TPD, preferentially inferior to 90 μmol/g-cat, more preferentially inferior to 80 μmol/g-cat. This can be obtained by performing a step of steaming the one or more zeolites before the contact of the catalyst composition with the feedstream.

The acidity of the zeolite catalyst was measured by $NH_3$-TPD. Generally, a temperature at which $NH_3$ is desorbed is an estimation of the strength of an acid site, i.e. higher the desorption temperature stronger is the acid site. The zeolite catalyst shows two $NH_3$-TPD peaks, a first one at 184° C. and a second at 363° C.

The one or more zeolites used in the first catalyst composition of the disclosure have a Si/Al molar ratio in the framework of the zeolite of at least 10 before the step of steaming, The Si/Al molar ratio before the step of steaming is typically ranging from 10 to 1500 as determined by TPD; preferably ranging from 80 to 1200; more preferably ranging from 150 to 1100 and most preferably from 800 to 1000.

The formation of extra-framework Al species is known to affect the pore structure and the porosity of the zeolite. Therefore, the removal of a large fraction of Al from the lattice leads to rearrangements of Si-T (tetrahedron) atoms and hence to the generation of large voids in the structure. The presence of such pores is crucial to obtain a high catalytic activity. Moreover, less aluminium also contributes to low coke formation and low ageing rates.

The steam treatment is conducted at elevated temperature, preferably in the range of from 300 to 800° C., more preferably in the range of from 400 to 750° C. and at a partial pressure of steam from 0.01 to 20 kPa, preferentially from 0.5 to 1.5 kPa. Preferably, the steam treatment is conducted at partial pressure of steam at least 1.5 kPa in the temperature range 300-450° C. If the temperature is above 450° C., the steam treatment is conducted in an atmosphere comprising the steam partial pressure below 1.5 kPa. The concentration of steam in the flow is between 1 to 100%, more preferably from 5 to 20% of steam. The diluent is a gas selected from the group of $N_2$, air, natural gas, $CO_2$ or a mixture of thereof. The steam treatment is preferably carried out for a period of from 0.1 to 200 hours, more preferably from 0.2 hours to 24 hours. As stated above, the steam treatment tends to reduce the amount of tetrahedral aluminium in the crystalline silicate framework, by forming alumina. The particular effect consists in reducing the strong Brønsted external acidity of the zeolites.

One or more zeolites used in the first catalyst composition of the disclosure have a Si/Al molar ratio in the framework of the zeolite of at least 80 after the step of steaming, The Si/Al molar ratio after the step of steaming is typically ranging from 80 to 1500 as determined by TPD; preferably ranging from 150 to 1200; more preferably ranging from 400 to 1100 and most preferably from 800 to 1000.

Optionally, following the steam treatment, an extraction step is performed to remove the partially dislodged alumina species by leaching. The leaching is performed by a monoprotic acid selected from the HCl, $HNO_3$, HBr, acetic or formic or with a complexing agent which tends to form a soluble complex with alumina. The complexing agent is preferably in an aqueous solution thereof. The complexing agent may comprise an organic acid such as citric acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. A particularly preferred complexing agent may comprise an amine, preferably ethylene diamine tetraacetic acid (EDTA) or a salt thereof, in particular, the sodium salt thereof.

Following the step of steaming, the catalyst is advantageously thereafter calcined in absence of steam (<1% of steam) at a temperature of from 550 to 700° C. at atmospheric pressure for a period of from 0.5 to 10 hours.

Optional Modification of the Steamed First Catalyst Composition with Phosphorus

Optionally, following the steaming step of the first catalyst composition, said steamed first catalyst composition is further modified by phosphorous under reduced or atmospheric pressure at a temperature from 10 to 400° C. A non-limiting source of phosphorus can be provided in an aqueous or non-aqueous medium.

In an embodiment, the non-limiting source of phosphorus is dissolved in a non-aqueous medium selected from the group containing ethanol, methanol or other alcohols.

The doping with a phosphorus-containing material consists of a steaming step followed by a leaching step using a solution of phosphoric acid ($H_3PO_4$) or using any acid solution containing the source of phosphorus. It is generally known by the persons in the art that steam treatment of zeolites results in aluminium that leaves the zeolite framework and resides as aluminiumoxides in and outside the pores of the zeolite. This transformation is known as the dealumination of zeolites. The treatment of the steamed zeolite with an acid solution results in the dissolution of the extra-framework aluminiumoxides. This transformation is known as leaching. Then the zeolite is separated, advantageously by filtration, and optionally washed. A drying step can be envisaged between the filtering and washing steps. The solution after the washing can be either separated, by way of example, by filtering from the solid or evaporated. The residual phosphorus-content is adjusted by the phosphorus concentration in the leaching solution, drying conditions, and washing procedure if any. This procedure leads to dealumination of zeolites and retention of phosphorus. Advantageously, at least 0.1 wt. % and up to 7.0 wt. % of phosphorus is retained after dealumination on zeolite. Both factors dealumination and the retention of phosphorus stabilize the lattice aluminium in the zeolitic lattice, thus avoiding further dealumination. This leads to higher hydrothermal stability, tuning of molecular sieves properties and adjustment of acid properties. The degree of dealumination can be adjusted by the steaming and leaching conditions.

The preferred techniques suitable for the modification by phosphorous are impregnation and chemical vapour deposition.

These techniques imply a minimum waste to treat and allow maintaining substantially all phosphorus on the catalyst.

In an embodiment, the phosphorus is introduced by a treatment of the catalyst in a solution containing a source of phosphorus at a temperature ranging between 25 and 100° C. for 0.1-96 h followed by filtering or evaporation.

In a preferred embodiment, the incipient wetness (IW) impregnation techniques are used. In these IW impregnation techniques, the phosphorus is introduced via impregnation using a limited amount of liquid water which is subjected to contact with the catalyst. This method is also known as dry impregnation.

Incipient wetness (IW) or incipient wetness impregnation (IWI) is a commonly used technique for the synthesis of heterogeneous catalysts. Typically, the precursor (phosphorus-containing compounds) is dissolved in an aqueous or organic solution. The volume of solution, which is used for dissolution of the precursor, is substantially the same as the pore volume of catalyst precursor containing both binder and zeolite. Then the precursor-containing solution is added to a catalyst precursor. Capillary action draws the solution into the pores. The catalyst can then be dried and calcined to drive off the volatile components within the solution, depositing the phosphorus on the catalyst surface.

The sample before impregnation can be dried or calcined. The impregnation could be performed at room or elevated temperature.

The adsorption capacity is typically measured by impregnating the dried extruded zeolite with water until the zeolite was completely wet. Weighing the zeolite before and after impregnation gives the absorption capacity according to formula (1):

$$\text{Absorption capacity (\%)} = \frac{\text{weight after impregnation} - \text{dry weight}}{\text{dry weight}} * 100 \quad (1)$$

In an embodiment, $H_3PO_4$ solution is used for impregnation.

Advantageously, a mixture of $H_3PO_4$ with their ammonium salts providing a pH of the aqueous solution higher than 2.0 is used for impregnation.

In an embodiment, the sources of phosphorus are substantially metal-free components, for example, $H_3PO_4$, ammonium phosphates or organic phosphorous-compounds. By way of example, this proportion can be below 1000 wt. ppm of the total weight of the phosphorous-containing material.

The amount of phosphorus in the catalyst can be from 0.1 to 30.0 wt. %, preferably from 0.3 to 9.0 wt. %. The amount of phosphorous on the catalyst is most preferably 2.0 wt. %.

Following the introduction of phosphorous, the catalyst is thereafter calcined and/or steamed at a steam partial pressure between 0.1 and 1 kPa at a temperature of from 550 to 750° C. at for a period of from 0.5 to 10 hours.

Steaming, in addition to trigger aluminium leaching also allows for the reduction of the number of acid sites.

The crystalline alumino-silicate oxide framework of the one or more zeolite has a portion of the aluminium that is substituted with boron and/or titanium. Preferentially, boron is used to substitute one or more aluminium atoms in the zeolite framework. Boron-substituted zeolite has a very weak acidity. The zeolite catalysts have a Si/(Al+B) molar ratio of at least 80, typically comprised between 100 and 1200, preferentially of 1000.

Optional Modification of the Phosphorous Modified Steamed Catalyst

The first catalyst composition modified with a phosphorous containing-material may contain a metal-containing material, which is preferably an alkaline earth metal-containing material. However, the alkaline earth metal-containing material is spatially separated from the zeolite, in which alkaline earth metal is strongly bounded with phosphorous. The said alkaline earth metal is selected from the group of beryllium, magnesium, calcium, strontium, barium and any mixtures thereof.

The metal-containing material that can be added to a catalyst composition modified with phosphorous is advantageously in the form of alkaline earth metal salts and comprise at least one inorganic anion selected preferably from the group of oxides, silicates, aluminates, titanates, phosphates, borates and borosilicates. Suitable silicate anions include $SiO_3^{2-}$, $SiO_4^{4-}$, $Si_2O_7^{6-}$ and so on. Suitable borate anions include $BO_2^-$, $BO_3^{2-}$, $B_2O_5^{4-}$, $B_4O_7^{2-}$, $B_6O_{11}^{4-}$, $B_{10}O_{19}^{8-}$ and so on. Suitable aluminate anions include $Al_2O_4^{2-}$, $AlO_4^{5-}$, $Al_6O_{18}^{18-}$ and so on. Suitable titanate anions include $TiO_3^{2-}$, $Ti_3O_7^{2-}$, $Ti_4O_9^{2-}$, $TiO_4^{4-}$ and so on. Suitable phosphate anions include $PO_4^{3-}$, $HPO_4^{2-}$, $H_2PO_4^-$, $P_nO_{3n+1}^{(n+2)-}$ and so on. Bi-, tri- and poly-metal silicates, borates and borosilicates containing one, two or more alkaline earth metals selected from the list above can be used too. The metal salt may also comprise other anions.

Examples of suitable alkaline earth metal salts that can be added to a catalyst composition modified with phosphorous include $MgrAl_2CO_3(OH)_{16}\cdot 4(H_2O)$ (hydrotalcite), $Mg_2B_2O_5\cdot H_2O$, $CaMgB_6O_{11}\cdot 6H_2O$ (hydroboracite), $Ca_2B_6O_{11}\cdot 5H_2O$ (colemanite), $Ca_4B_{10}O_{19}\cdot 7H_2O$, $Mg(BO_2)$ .8$H_2O$, Ca($BO_2$).2$H_2O$, $Ba_6B_{10}$.4$H_2O$, $CaSi_6O_{17}(OH)_2$ (xonotlite), CaMg($Si_2O_6$)$_x$, $Mg_2$($Si_2O_6$)$_x$, $CaAl_2Si_2O_8$, $Mg_4Si_6O_{15}(OH)_2$.6$H_2O$ (sepiolite), $(Mg,Al)_2Si_4O_{10}(OH)$.4$H_2O$ (palygorskite or attapulgite) and mixtures thereof.

A further example of suitable alkaline earth metals that can be added to a catalyst composition modified with phosphorous is Mg($NO_3$)$_2$ (magnesium nitrate).

Before mixing with the molecular sieve, said alkaline earth metal salts may be modified by calcination, steaming, ion-exchange, impregnation, and/or phosphatation. Said alkaline earth metal salts can be an individual compound or can be a part of mixed compounds, for example, mixed with mineral, natural or chemical fertilizer.

The catalyst composition of the present disclosure modified with at least one phosphorous-containing material and at least one alkaline earth metal-containing material has for effect to increase the selectivity to olefins (i.e. acyclic C3-C6 olefins) and to decrease subsequently the rate of the alkane formation (i.e. C3-C6 alkanes).

In a preferred embodiment, the catalyst composition modified with phosphorous further comprises from 1 to 50 wt. % of hydrotalcite as based on the total weight of the catalyst composition; with preference from 5 to 25 wt. %. The hydrotalcite is of the formula $Mg_6Al_2CO_3(OH)_{16}$.4($H_2O$).

In another preferred embodiment, the one or more zeolites are doped with both at least one phosphorus-containing material and with at least one alkaline earth metal-containing material, preferably at least one magnesium-containing material and/or at least one calcium-containing material.

The Shaping of the Catalyst with a Binder

According to the disclosure, one or more zeolites are shaped with a binder, which is an inorganic material, and preferentially silica. The zeolites shaped with the binder forms a catalyst composition, and the catalyst composition of the present disclosure preferably comprises at least 10 wt. % of a binder, at most 40 wt. % as based on the total weight of the first catalyst composition and at most 40 wt. %. Typically, the first catalyst composition of the present disclosure comprises between 20 wt. % and 25 wt. % of a binder as based on the total weight of the first catalyst composition.

The preferred binder is selected from silica, alpha-alumina, clays, alumina phosphates, calcium phosphates, magnesium phosphates, and mullite. Most preferentially, the binder is silica.

The binder preferably does not contain any aluminium compounds, such as alumina. This is because as mentioned above the preferred catalyst for use in the disclosure is de-aluminated by steaming to increase the Si/Al molar ratio of the crystalline silicate. The presence of alumina in the binder, as well as the presence of hydrogen halides, may lead to the re-alumination of the zeolite. The presence of aluminium in the binder would also tend to reduce the olefins selectivity of the catalyst and to reduce the stability of the catalyst over time.

The binder is present in an amount of at least 10 wt. % as based on the total weight of the first catalyst composition; preferably in an amount of at least 20 wt. %, most preferably in an amount of 30 wt. %, even more preferably in an amount of at least 40 wt. %, and most preferably in an amount of at least 50 wt. %.

Non-limiting examples of silicon sources suitable for the binder of the catalyst composition include silicates, precipitated silicas (for example, Zeosil® available from Rhodia), fumed silicas (for example, Aerosil®200 available from Degussa Inc., New York, N.Y.), silicon compounds (such as tetraalkyl orthosilicates, for example, tetramethyl orthosilicate (TMOS) and tetraethylorthosilicate (TEOS)), colloidal silicas or aqueous suspensions thereof (for example Ludox® HS-40 available from E.I. du Pont de Nemours, Wilmington, Del.), silicic acid, alkali-metal silicate, or any combination thereof.

Other suitable forms of amorphous silica include silica powders, such as Ultrasil® VN3 SP (commercially available from Degussa).

Other non-limiting examples of a suitable solid silica source are special granulated hydrophilic fumed silica, mesoporous silica and high surface area precipitated silica SIPERNAT® from Evonik, Hi-Sil 233 EP (available from PPG Industries) and Tokusil (available from Tokuyama Asia Pacific).

In addition, suitable amorphous silica sources include silica sols, which are stable colloidal dispersions of amorphous silica particles in an aqueous or organic liquid medium, preferably water.

Non-limiting examples of commercially available silica sols include those sold under the tradenames Nyacol® (available from Nyacol Nano Technologies, Inc. or PQ Corp.), Nalco (available from Nalco Chemical Company), Ultra-Sol (available from RESI Inc), Ludox® (available from W.R. Grace Davison), NexSil™ (available from NNTI).

Many silica sols are prepared from sodium silicate and inevitably contain sodium. It is, however, found that the presence of sodium ions can cause sintering of the silica body at high temperature and/or affect catalytic performance. Therefore, if silica sols containing sodium are used, a step of ion exchange may be required to reduce or remove sodium. To avoid carrying out ion exchange steps, it is convenient to use silica sols that contain very little or, ideally, no detectable traces of sodium and have a pH value of less than 7. Most preferably, the silica sol used in the process is slightly acidic with or without polymeric stabilizers. Non-limiting examples of silica sols that contain no detectable traces of sodium include Bindzil® 2034D1, Levasil® 200, Nalco 1034A, Ultra-Sol 7H or NexSil™ 20A.

In some case, silica dispersion prepared with alkylammonium might be useful. Non-limiting examples of commercially low sodium silica sols stabilized by ammonia or alkylammonium cations include LUDOX® TMA (available from W.R. Grace Davison) or VP WR 8520 from Evonik.

The silica sols with higher $SiO_2$ content than 30 wt. % and even up to 50 wt. %, for example, W1250, W1836, WK341, WK7330 from Evonik are particularly preferred.

The preferred source of silicon is a silica sol or a combination of silica sol with precipitated or fumed silica.

The Second Catalyst Composition

The second catalyst composition is a catalyst suitable for an olefin cracking reaction. Preferred catalysts for the olefin cracking reaction can be selected from one or more zeolites and/or one or more clays.

With preference, said cracking catalyst comprises one or more zeolites selected from silicalites from the MFI family, crystalline silicate from the MFI family with a Si/Al atomic ratio of at least 180, crystalline silicate from the MEL family with a Si/Al atomic ratio ranging between 150 and 800, and/or phosphorous-modified zeolite from the MFI, MEL, FER, MOR family and/or phosphorous-modified clinoptilolite.

In one embodiment, said cracking catalyst comprises one or more zeolites selected from silicalites from the MFI family, optionally with a silica binder.

Examples of suitable catalysts were disclosed in the international patent application published WO2004/048299.

Examples of crystalline silicate from the MFI family are ZSM-5 and silicalite. An example of crystalline silicate from the MEL family is ZSM-11, which is known in the art. Other suitable non-limiting examples are boralite D and silicalite-2, or any mixtures thereof.

The preferred crystalline silicates have pores or channels defined by ten oxygen rings and a high Si/Al atomic ratio. The catalyst having a high Si/Al atomic ratio may be manufactured by removing aluminium from a commercially available catalyst. The commercially available catalysts may be modified by steaming to remove at least part of inter-framework aluminium followed by leaching step to remove external aluminium.

The cracking catalyst can be formulated with a binder, preferably an inorganic binder, and shaped to the desired shape, e.g. extruded pellets. The binder is an inorganic material selected from clays, silica, metal oxides. Preferably, the binder content ranges from 5 to 50% by weight, more typically from 15 to 35% by weight, based on the weight of the cracking catalyst. More preferably, the binder is a silica binder.

The cracking catalyst can be subjected to a steaming step before step (d).

The olefin cracking reaction is known per se. It has been described in EP1035915, EP1036133, EP1036134, EP1036135, EP1036136, EP1036137, EP1036138, EP1036139, EP1190015, EP1194500, EP1194502, and EP1363983. The content of which is incorporated in the present description.

The Process

When the catalysts are ready, the first catalyst composition is filled in a first reaction zone and the second catalyst composition is filled in a second reaction zone, the first reaction zone being upstream of the second reaction zone. The two reaction zones can be two separate reactors fluidly connected or two separate parts of one single reactor. Said separate reactors or said single reactor can be a fixed bed, a fluidized bed or another suitable reactor. Preferentially it can be a fixed-bed tubular reactor. In this case, the diameter of the inner tube may be of 11 mm.

The process comprises the step of providing a feedstream to be contacted by the first catalyst, the feedstream comprises one or more alkyl halides; optionally, diluted in at least one diluent.

The first product stream produced by contacting the feedstream with said first catalyst composition is then directed to a separate vessel or a separate reactor and is contacted by the second catalyst.

In a preferred embodiment, the alkyl of said alkyl halides is methyl, ethyl or propyl, preferentially methyl, and in that the halogen of said alkyl halides is F, Cl, Br, or I, preferentially Br.

The alkyl halide comprised in the feedstream can optionally comprise 1, 2, 3 or 4 halogens. Advantageously, the alkyl halide comprised in the feedstream comprises 1 halogen and is a monohalo-alkyl. In this case, it is advantageous that the halide is a bromide.

The one or more alkyl halides optionally comprises up to 10 wt. % of alkyl dihalide.

With preference, the alkyl halide is methyl bromide.

In a preferred embodiment, a diluent can be added in the feed comprising said one or more alkyl halides. Said diluent can be one or more of hydrogen halides, steam, C1-C4 alkanes, alkanols, CO, $CO_2$, $N_2$ or monocyclic aromatics (e.g. benzene, toluene and/or xylene), preferentially $N_2$.

Methane can also be present in the feedstream.

With preference, in the first vessel or in the first reactor, the weight of feed comprising flowing per unit of weight of the catalyst per hour (weight hourly space velocity, WHSV) is comprised between 0.1 $h^{-1}$ and 100 $h^{-1}$, preferentially between 1.0 $h^{-1}$ and 15 $h^{-1}$. More preferably, WHSV is comprised between 1.5 $h^{-1}$ and 10 $h^{-1}$. Even more preferably, WHSV is comprised between 2.0 $h^{-1}$ and 6.0 $h^{-1}$. This means that the first catalyst of the present disclosure can convert the weight of the feed that is superior to the amount of the first catalyst present in the first reactor.

In a preferred embodiment, the first reaction conditions of step (c) include a reaction temperature ranging from 150° C. to 380° C.; preferably ranging from 250° C. to 350° C.; more preferably ranging from 260° C. to 340° C., even more preferably ranging from 280° C. to 320° C., most preferably at a temperature of 300° C.

The use of a relatively low temperature is advantageous (for safety reasons notably). In US 2008/0188701 described above, the reduction in the formation of ethylene (5.96%) has been achieved at a temperature of 450° C. with a catalyst composition comprising 50 wt. % SAPO-11 molecular sieve and 50 wt. % of alumina as a binder. As it will be demonstrated in the experimental part of the present disclosure, using one or more zeolites with a binder allows for obtaining poor ethylene formation (as less than 0.5%) at a temperature of only 280° C. In the best example, the selectivity in ethylene has been measured to be less than 0.01% at a temperature of 320° C., namely 130° C. below the temperature described in the prior art for a similar reaction (although not reaching the selectivity demonstrated in the present disclosure). A low selectivity to aromatic compounds (<15%) is also obtained during the conversion of alkyl halides to C3-C6 olefins.

Preferably, the first reaction conditions of step (c) include a pressure ranging from 10 kPa to 500 kPa, preferably ranging from 20 kPa to 300 kPa.

A first product stream is obtained. The first product stream is an effluent comprising C3-C6 olefins, hydrogen halide, unreacted one or more alkyl halides, alkane and higher hydrocarbons and optionally said diluent. The selectivity to C3-C6 olefin is of at least 70%, preferentially of at least 75%.

In a preferred embodiment, the hydrogen halides are removed from said first product stream before the cracking step, preferentially by gas purification techniques, by directing said first product stream through a wet scrubber (e.g. water scrubber or a water stripper) through an acetic acid extractive distillation vessel, or by an oxidation unit that contains preferentially a metal oxide reactor bed. In another preferred embodiment, the unreacted one or more alkyl halides are recovered before the cracking step, preferentially by distillation of the first product stream. The unreacted one or more alkyl halides can be preferentially reinjected into the said feedstream of step (a). In yet another preferred embodiment, the aromatics are removed from said first product stream before the cracking step, preferentially by distillation of the first product stream. These purification steps promote the cracking step since the potential impurities (hydrogen halide, unreacted alkyl halide and/or aromatics) that could prevent the good functioning of the cracking step are removed.

In a preferred embodiment, at least part of C2 hydrocarbons separated from the effluent of homologation reactor or cracking reactor and could be reinjected into said feedstream of step (a).

In a preferred embodiment, at least part of C4 hydrocarbons could be separated from the effluent of homologation reactor or cracking reactor and could be reinjected into said feedstream of step (a).

The first product stream is then contacted with the second catalyst composition under second reaction conditions.

With preference, in the second vessel or in the second reactor, the weight of feed comprising flowing per unit of weight of the catalyst per hour (weight hourly space velocity, WHSV) is comprised between 0.1 $h^{-1}$ and 100 $h^{-1}$, preferentially between 1.0 $h^{-1}$ and 15 $h^{-1}$. More preferably, WHSV is comprised between 1.5 $h^{-1}$ and 10 $h^{-1}$. Even more preferably, WHSV is superior than 1 $h^{-1}$ but lower or equal to 100 $h^{-1}$. This means that the second catalyst of the present disclosure can convert a weight of the feed that is superior to the amount of the second catalyst present in the second reactor.

In a preferred embodiment, the second reaction conditions of step (d) include a reaction temperature ranging from 500° C. to 600° C.; preferably ranging from 510° C. to 590° C.; more preferably ranging from 520° C. to 580° C.

Preferably, the second reaction conditions of step (d) include a pressure ranging from 10 kPa to 500 kPa, preferably ranging from 20 kPa to 300 kPa.

A second product stream is thus obtained. The second product stream is an effluent comprising mainly ethylene and propylene. One or more side products may be produced as well, such as methane, ethane, propane, C4+ olefins, C5+ linear hydrocarbons and BTX).

In a preferred embodiment, at least part of said second product stream could be recycled back to the cracking reactor of step (d).

In an embodiment, the step (d) of contacting the first product stream with the second catalyst composition is followed by a step (e) of performing a separation of ethylene and propylene from the second product stream. The step (e) may be preferentially carried out by performing at least one compression and/or at least one distillation of said second product stream.

In a preferred embodiment, the aromatics are removed from said second product stream before the recycling.

Figure 4:
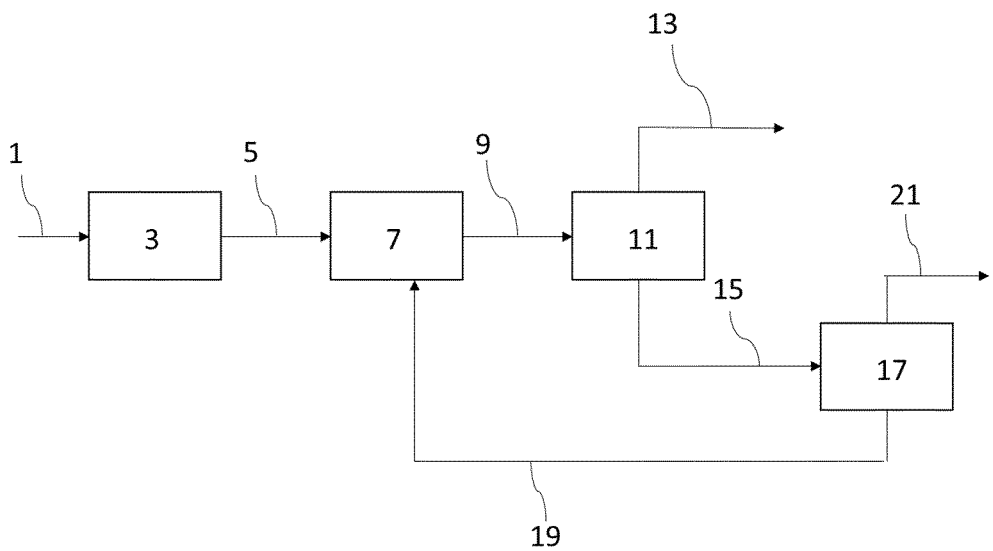
FIG. 4 shows a first possible implementation of the process of the present disclosure.
Figure 5:
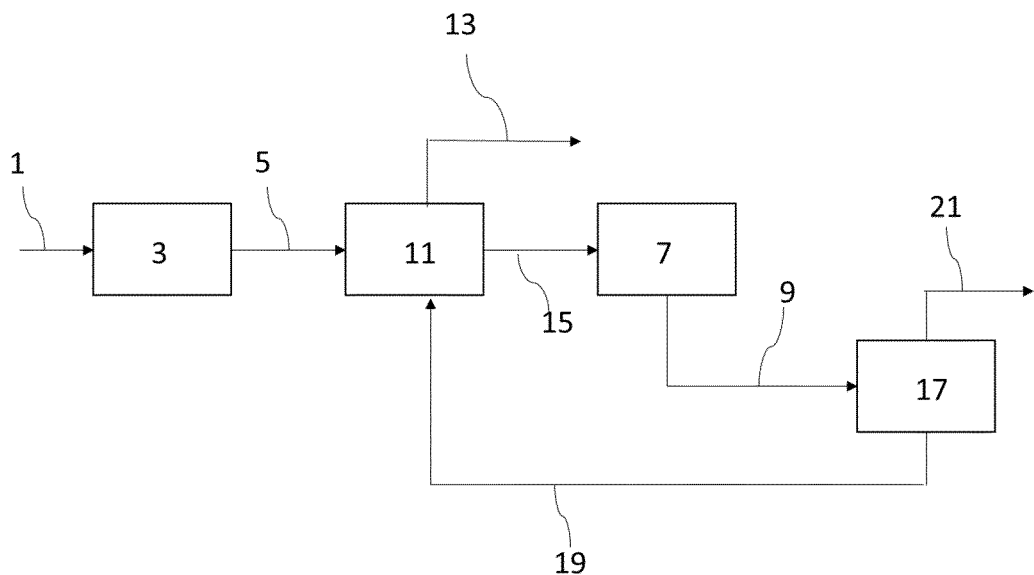
FIG. 5 shows a second possible implementation of the process of the present disclosure.
Figure 6:
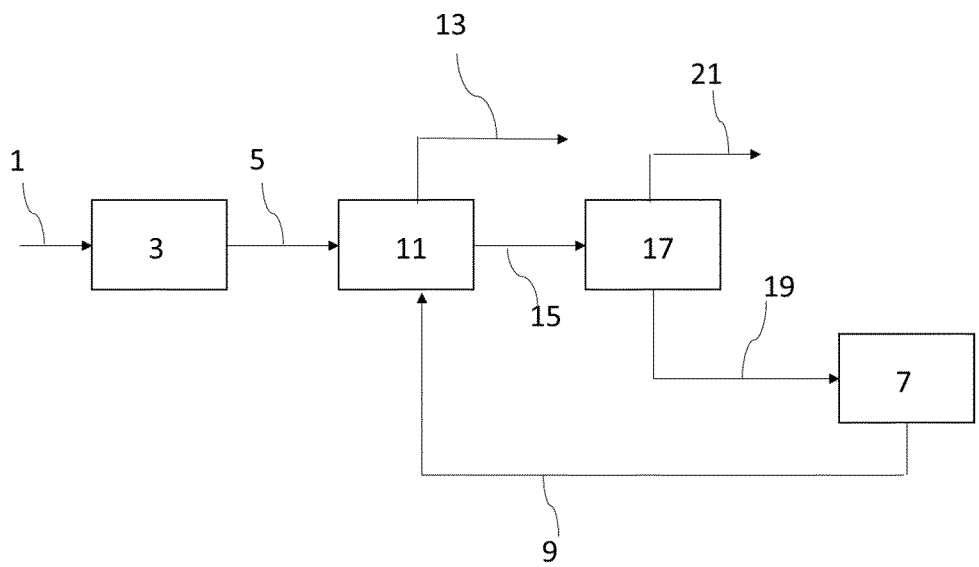
FIG. 6 shows a third possible implementation of the process of the present disclosure.

The FIGS. 4, 5 and 6 depict some of the possible implementations of the process of the disclosure:

A feedstream 1 comprising methyl bromide as alkyl halides and hydrogen bromide as diluent is introduced into the first reaction zone 3. The first catalyst composition in the first reaction zone 3 converts said feedstream 1 into a first product stream 5 comprising C2-C9 hydrocarbons (with a selectivity of at least 70% into acyclic C3-C6 olefins), and also methane. The first product stream 5 also comprises hydrogen bromide and unreacted methyl bromide. As shown in FIG. 4, the first product stream 5 can be directed in totality through the second reaction zone 7, to produce a second product stream 9 that is then treated in a separation unit 11, for example, a compression or an extractive distillation unit. This treatment in the separation unit 11 affords a stream 13, comprising essentially ethylene and propylene, and a C4+ stream 15 that can be further passed through an additional separation unit 17, preferably a deoctanizer. From said additional separation unit 17, the high boiling point fraction 21, preferably comprising C8+ compounds, is recovered and can be valorised as fuel. The low boiling point fraction 19, comprising C4-C7 compounds, is also recovered and recycled to the second reaction zone 7.

Alternatively, as shown in FIG. 5, the first product stream 5 is directed in a separation unit 11, to afford a C4+ stream 15 which is then directed in the second reaction zone 7. The second product stream 9 is then treated through an additional separation unit 17, which allows to recover a low boiling point fraction 19 comprising essentially ethylene and propylene but also C4-C7 compounds. The low boiling point fraction 19 is redirected through a separation unit 11, which allows for the separation of the stream 13 comprising essentially ethylene and propylene and which can be the same or different of the first one, preferably it is the same. In this implementation, the C4-C7 compounds of the low boiling point fraction 19 can also be recycled. Alternatively yet, and as shown in FIG. 6, the first product stream 5 is directed in a separation unit 11, to afford a C4+ stream 15 which is then directed through an additional separation unit 17, preferably a deoctanizer. This allows for removing a high boiling point fraction 21, preferably comprising C8+ compounds, that can be valorised as fuel, and to allow the low boiling point fraction 19, comprising essentially C4-C7 compounds, to go through the second reaction zone 7 to be subjected to the cracking step. The second product stream 9 generated from said second reaction zone 7, which comprises essentially ethylene and propylene, but also C4+ compounds, is then redirected to a separation unit 11 which allows for the separation of the stream 13 comprising essentially ethylene and propylene and which can be the same or different of the first one, preferably it is the same. With this configuration, the C4+ compounds are thus separated from the second product stream 9 and can be recycled.

Test and Determination Methods

The conversion of the one or more alkyl halides ($X_{RX}$) is determined according to formula (1):

$$X_{RX} = \frac{[RX]^i - [RX]^f}{[RX]^i} \times 100 \tag{1}$$

wherein $[RX]^i$ and $[RX]^f$ are the molar amount of the alkyl halide RX in the (initial) feed and in the (final) effluent (or product stream) respectively.

The selectivity in methane (C1) is determined according to formula (2):

$$S_{methane} = \frac{[CH_4]}{[CH_4] + 2[C_2H_4] + 2[C_2H_6] + 3[C_3H_6] + 3[C_3H_8] + 4[C_4H_8] + 4[C_4H_{10}] + \cdots} \times 100 \tag{2}$$

wherein the numerator is the carbon adjusted molar amount of methane and the denominator is the sum of all the carbons adjusted molar amount of all hydrocarbon in the effluent.

The selectivity in ethylene (C2=) is determined according to formula (3):

$$S_{ethylene} = \frac{2[C_2H_4]}{[CH_4] + 2[C_2H_4] + 2[C_2H_6] + 3[C_3H_6] + 3[C_3H_8] + 4[C_4H_8] + 4[C_4H_{10}] + \cdots} \times 100 \tag{3}$$

wherein the numerator is the carbon adjusted molar amount of ethylene and the denominator is the sum of all the carbons adjusted molar amount of all hydrocarbons in the effluent.

The selectivity in propylene (C3=) is determined according to formula (4):

$$S_{propylene} = \frac{3[C_3H_6]}{[CH_4] + 2[C_2H_4] + 2[C_2H_6] + 3[C_3H_6] + 3[C_3H_8] + 4[C_4H_8] + 4[C_4H_{10}] + \cdots} \times 100 \quad (4)$$

wherein the numerator is the carbon adjusted molar amount of propylene and the denominator is the sum of all the carbons adjusted molar amount of all hydrocarbons in the effluent.

Similar equations (not shown) are used for determining the selectivity in butylene, pentene, hexene, and also for the corresponding alkanes.

The selectivity in aromatics is determined according to formula (5):

$$S_{aromatics} = \frac{6[C_6H_6] + 7[C_7H_8] + 8[C_8H_{10}])}{[CH_4] + 2[C_2H_4] + 2[C_2H_6] + 3[C_3H_6] + 3[C_3H_8] + 4[C_4H_8] + 4[C_4H_{10}] + \cdots} \times 100 \quad (5)$$

wherein the numerator is the carbon adjusted molar amount of aromatics (benzene, toluene and xylene) and the denominator is the sum of all the carbons adjusted molar amount of all hydrocarbons in the effluent.

Temperature Programmed Desorption (TPD) is the method of observing desorbed molecules from a surface when the surface temperature is increased. It has been performed by following the heating sequences I, and Ill shows on FIG. 2, respectively corresponding to activation, saturation and analysis. In brief, in the first step (marked as I on FIG. 2), starting from room temperature (25° C.) under a flow of helium (rate 50 cc/min), the temperature has been gradually increased to 600° C. at a rate of 20° C./min. After 1 hour at 600° C., the zeolite sample is considered as being activated and the temperature is then gradually decreased to 100° C. at a rate of 10° C./min. Then, in the second step (marked as II on FIG. 2) during 3 hours, the temperature is maintained at 100° C. and in the first 1 hour, 10% of ammonia ($NH_3$) is added to the helium flow (which is decreased to 30 cc/min). The surface of the zeolite is thus saturated with the molecules of ammonia that are going to be adsorbed onto the surface. The last 2 hours of the temperature threshold at 100° C., the initial flow of helium is reinstated. Then, in the third step (marked as Ill in FIG. 2) the temperature is increased again to 600° C. at a rate of 10° C./min to desorb the ammonia. The sample is maintained at 600° C. for an additional one hour. It is highlighted that the skilled person could use different parameters (time, temperature, flow rate, carrier gas) to perform the method. The measurement of the amount of ammonia using a thermal conductivity detector allows to recognize the different adsorption conditions of the ammonia onto the zeolite and allows for obtaining a description of the surface of the zeolite, such as the number of acid sites.

For the measurement of the amount of ammonia in the zeolite sample, the sample is dried, corrected to loss of ignition at 200° C.

In order to determine the Si/Al molar ratio of the zeolites sample by $NH_3$-TPD method, the measurement of the amount of aluminium in the framework is based on the assumption that one $NH_3$ molecule interacts with one Brønsted or Lewis acid site. As the sample of zeolite is saturated at 100° C. with dry $NH_3$, all kind of physisorption (physical sorption on sites non-linked with Al in the framework) is avoided to limit the polydentate interactions (interaction of the acid sites with several molecules of ammonia). Subsequently, only the strongly adsorbed $NH_3$ molecules on the acid sites are quantified. This means that by the measurement of the amount of the strongly adsorbed $NH_3$ in TPD, it is possible to obtain the amount of the acid sites linked with Al in the framework of zeolite. In general, one atom of aluminum in the framework of zeolite generates one acid site. The number of moles (n) of $NH_3$ consumed thus corresponds to the amount of Al atoms, as determined by the following equation:

$n(Al_2O_3) = n(NH_3)/2$ [mol].

The rest would correspond to $SiO_2$, as calculated according to the following equation when the mass of the dried zeolite sample is 1 g:

$n(SiO_2) = (1[g] - Mr(Al_2O_3) * n(NH_3)/2)/Mr(SiO_2)$, $Mr$ standing for molecular mass.

Gas chromatography experiments were carried out to determine quantitatively the selectivity of the reaction. It was performed on a silica BOND column (60 m×0.32 mm) using Agilent operated by ChemStation software.

The metal content was determined by X-ray fluorescence (XRF) spectroscopy using an Orbis Micro-EDXRF spectrometer equipped with a Rh source (15 kV, 500 μA) and a silicon drift detector.

The Si/Al atomic ratio corresponds to the amount of $SiO_2$ divided by the amount of $Al_2O_3$ taking into account the fact there are two atoms of aluminium for one atom of silicon. The silica to alumina ratio (also stated as SAR) corresponds to the amount of $SiO_2$ divided by the amount of $Al_2O_3$ notwithstanding the proportion of the Si atoms over the Al atoms in the chemical formula of the zeolite. Therefore, the value of the SAR always corresponds to twice the value of the Si/Al atomic ratio.

EXAMPLES

The embodiments of the present disclosure will be better understood by looking at the different examples below.

Examples 1 to 3 concern step (c) of the process according to the disclosure.

Example 4 is an example showing the results of the additional step of cracking, corresponding to step (d) of the process of the present disclosure.

Example 1

A sample of commercial zeolite CBV28014 from Zeolyst (Si/Al atomic ratio of 140), ZSM-5, was shaped with a silica binder in a ratio 80:20. The extruded sample was calcined for 2 h at 600° C. followed by steaming at 750° C. for 1 h in 50% steam. The catalyst composition comprising steamed and acidified ZSM-5 to form a silicalite from the MFI family with $SiO_2$ binder, showing the final Brønsted acid sites concentration of 81 μmol/g-cat (measured by TPD-$NH_3$), was thus prepared.

Figure 2:
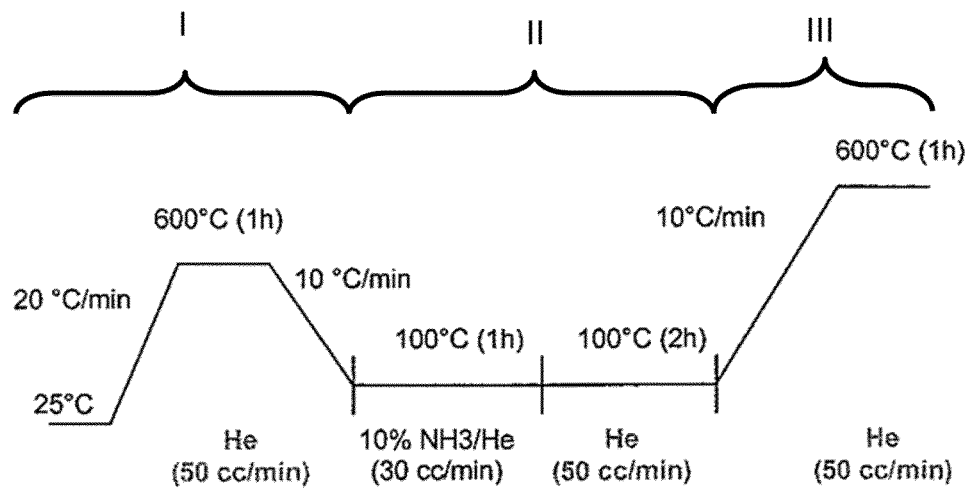
FIG. 2 shows an example of the settings of the temperature-programmed desorption (TPD) method.
Figure 3:
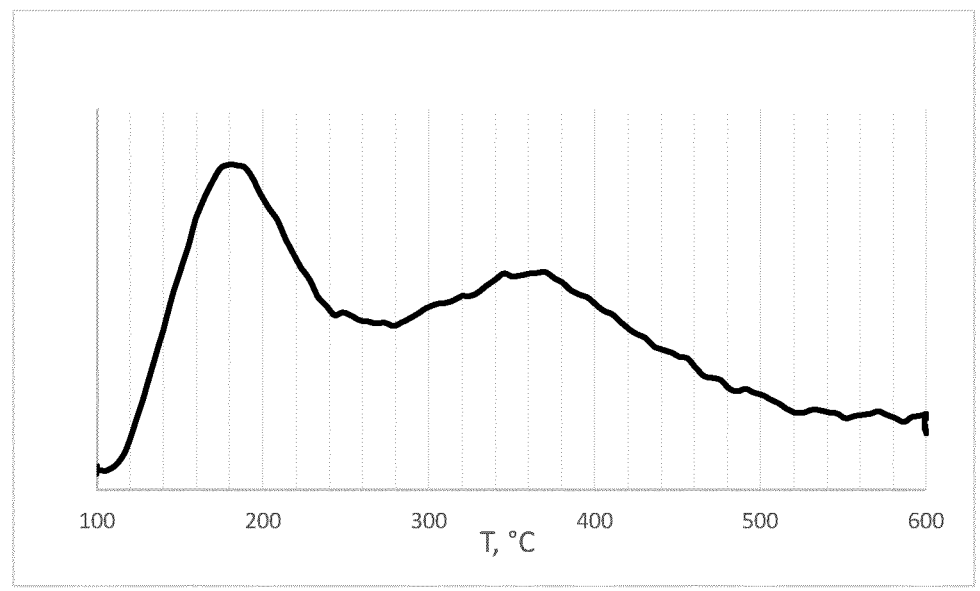
FIG. 3 shows the $NH_3$-TPD profile of the catalyst of the first catalyst composition according to the disclosure.

The particulars of said catalyst composition, as determined by the TPD (Temperature Programmed Desorption) test, show that the acid site density (μmol/g-cat), measured from the amount of $NH_3$ desorbed, is of 32 μmol/g-cat for the first peak and 49 μmol/g-cat for the second peak (see FIG. 2). Therefore, the Brønsted acid sites are present in a concentration of 81 μmol/g-cat.

ZSM-5 aluminosilicate was steamed and acidified to form a silicalite from the MFI family having a Si/Al molar ratio of 1000. With a $SiO_2$ binder, it was used as a catalyst for $CH_3Br$ conversion in a fixed-bed tubular reactor at a temperature of 280° C. for a period of 48 h or longer. For the catalytic test, the powder was pressed, then crushed and seized between 35-45 mesh screens. In the test, a fresh load of the seized catalyst of 10 mL (i.e. 6.3 g) was loaded in a reactor (11 mm inner diameter) and the catalyst was preactivated in an $N_2$ flow at 525° C. for 6 h. Then, the temperature was decreased to 280° C. and pure $N_2$ flow was replaced with the flow of $N_2/CH_3Br$ 10/1 mol. with WHSV of $CH_3Br$/catalyst of 1.6 $h^{-1}$. The reactor pressure was 2 barg during the test run.

The results are reported in table 1 and compared to prior art results given in US2016/0200642.

TABLE 1

Conversion and selectivity results: example 1 vs. prior art

| Catalyst | Example 1 silicalite[#] with $SiO_2$ binder | Comparative Example 1[(1)] HZMS-5 | Comparative Example 2[(1)] silicalite[#] |
|---|---|---|---|
| SAR[†] | >150 | 30 | 1192 |
| Temperature (° C.) | 280 | 350 | 350 |
| Pressure | 2 barg | 0.2 barg | 0.2 barg |
| WHSV ($h^{-1}$) | 1.6 | 0.9 | 0.9 |
| $N_2/CH_3Br$ (mol/mol) | 10/1 | — | — |
| $N_2/CH_3Cl$ (mol/mol) | — | 4/1 | 4/1 |
| Partial pressure of $CH_3X$ | 0.27 bar | 0.24 bar | 0.24 bar |
| Products | Selectivity (%) | | |
| methane | <0.05 | n.d. | n.d. |
| ethane | <0.01 | 66.7 [(2)] | 0 |
| C3 | <0.5 | | |
| C4 | 7.2 | | |
| C5 | <0.01 | 2.4 [(3)] | 7.4 |
| C6 paraffins | 0.8 | | |
| C6= | 25.5 | | |
| C5= | 37.7 | | |
| C4= | 10.8 | 6.2 | 21.7 |
| C3= (propylene) | 7.9 | 2.2 | 60.2 |
| Bromides | 0.3 | n.d. | n.d. |
| Aromatics | 2.1 | 17.3 | 0 |
| C2= (ethylene) | <0.5 | 3 | 6.5 |
| Total selectivity to alkanes | <8.57 | <69.1 | <7.4 |
| Conversion | >99 [(4)] | 96.6 [(4)] | 8.6 [(4)] |
| | Yield (%) | | |
| Yield of C3-C6 olefins | 81.1 | <10.4 | <7.7 |
| Yield of ethylene | <0.5 | 2.9 | 0.6 |
| Yield of ethylene and propylene | <8.4 | <5.1 | <5.8 |
| Yield of aromatics | 2.1 | 16.7 | 0 |

[#]silicalite from the MFI family.
[†]as defined from TPD measurement.
[(1)]Comparative Example 1 corresponds to example 1 of US2016/0200642 and comparative example 2 corresponds to example 8 of US2016/0200642.
[(2)] Data for C2-C4 alkanes.
[(3)] Data for C5+ hydrocarbons.
[(4)]Conversion measured after 20 hours on stream.

From the results, it can be seen that the catalyst composition comprising silicalite from the MFI family shaped with a binder and the process of the disclosure achieve a high yield to 03-06 olefins whereas, in the prior art, such a yield is quite low. Also, the disclosure allows a low yield to ethylene (<0.5%) as well as a low yield to aromatics compounds (<15%).

Example 2

A sample of zeolite ZSM-5 (CBV2314 from Zeolyst) (Si/Al atomic ratio of about 12) in $NH_4$-form was shaped with a silica binder in a ratio 80:20. The extruded sample was calcined for 2 h at 600° C. followed by steaming at 600° C. for 2 h in 50% steam. Then the sample was incipient wetness impregnated with an aqueous solution containing phosphoric acid to introduce 2.3 wt. % of phosphorous. The impregnated solid was dried for 16 h at 110° C. and steamed at 750° C. for 1 h in 100% of steam.

The results are reported in table 2.

Example 3

The sample of catalyst from Example 1 was modified by impregnation with phosphoric acid, $H_3PO_4$, and magnesium nitrate, $Mg(NO_3)_2$ and utilized as a catalyst for $CH_3Br$ conversion in a fixed-bed tubular reactor at a temperature of 320° C. for a period of 48 h or longer. For the catalytic test, the powder was pressed, then crushed and seized between 35-45 mesh screens. In the test, a fresh load of the seized catalyst of 10 mL (i.e. 6.6 g) was loaded in a reactor (11 mm inner diameter) and the catalyst was pre-activated in an $N_2$ flow at 525° C. for 6 h. Then, the temperature was decreased to 320° C. and pure $N_2$ flow was replaced with the flow of $N_2/CH_3Br$ 10/3 mol/mol with WHSV of $CH_3Br$/catalyst of 5 $h^{-1}$. The reactor pressure was 2 barg during the test run.

The results are reported in table 2.

TABLE 2

Conversion and selectivity results: examples 2 and 3

| Catalyst | Example 2 P-Silicalite[#] with $SiO_2$ binder | Example 3 Mg—P-Silicalite[#] with $SiO_2$ binder |
|---|---|---|
| SAR[†] | >150 | >150 |
| Temperature (° C.) | 280 | 320 |
| Pressure (barg) | 2 | 2 |
| WHSV ($h^{-1}$) | 5 | 5 |
| $N_2/CH_3Br$ (mol/mol) | 10/3 | 10/3 |
| Product | Selectivity (%) | |
| methane | <0.1 | <0.1 |
| ethane | <0.01 | <0.01 |
| C3 | <0.1 | 0.4 |
| C4 | 5.8 | 2.6 |
| C5 | 0.6 | 0.3 |
| C6 paraffins | 0.5 | 0.3 |
| Total selectivity to alkane | <7.11 | <3.71 |
| ethylene | <0.01 | <0.1 |
| C3= (propylene) | 16.1 | 19.9 |
| C4= | 24.7 | 28.1 |
| C5= | 14.6 | 14.7 |
| C6= | 18.3 | 21.7 |
| Aromatics | 4.1 | 1.4 |
| Bromides | 0.4 | 0.2 |
| Conversion | 20 | 23 |
| | Yield (%) | |
| Yield of C3-C6 olefins | 14.7 | 19.4 |
| Yield of ethylene | <0.002 | <0.023 |
| Yield of ethylene and propylene | <3.3 | <4.6 |
| Yield of aromatics | 0.8 | 0.3 |

[#]silicalite from the MFI family.
[†]as defined from TPD measurement.

The decrease in the conversion rate from examples 1 (>99%) compared to examples 2 and 3 (<25%) is explained by a higher velocity used in the reaction (WHSV>5 h$^{-1}$).

It is noted that the lowest yield in the production of C3-C6 olefins (14.7%) achieved in example 2 is still higher than the yield shown in the comparative example 1 (<10.4%) wherein HZMS-5 with low SAR of 30 was used. Using the best conditions of the process, namely using a catalyst composition comprising silicalites, magnesium and phosphorus, a yield of 19.4% (example 3) can be achieved while minimizing the production of ethylene and aromatics.

The modification of the one or more zeolites with phosphorous, and ultimately with a combination of phosphorous and magnesium has allowed for obtaining a steady conversion with high selectivity for light products for 48 hours with a steamed catalyst.

Example 4: Stability Studies of the Catalyst

Using the catalyst composition of example 1, namely a silicalite from the MFI family with SiO$_2$ as a binder, the conversion plot of CH$_3$Br into C3-C6 olefins over time was obtained.

The conditions reaction for this stability experiment are indicated in table 3:

TABLE 3

| Conditions reaction of example 4 | |
| --- | --- |
| SAR† | >150 |
| Temperature (° C.) | 280 |
| Pressure | 6 barg |
| WHSV (h$^{-1}$) | 2.0 |
| N$_2$/CH$_3$Br (mol/mol) | 7/3 |
| Partial pressure of CH$_3$X | 2.1 bara |

†as defined from TPD measurement

Figure 7:
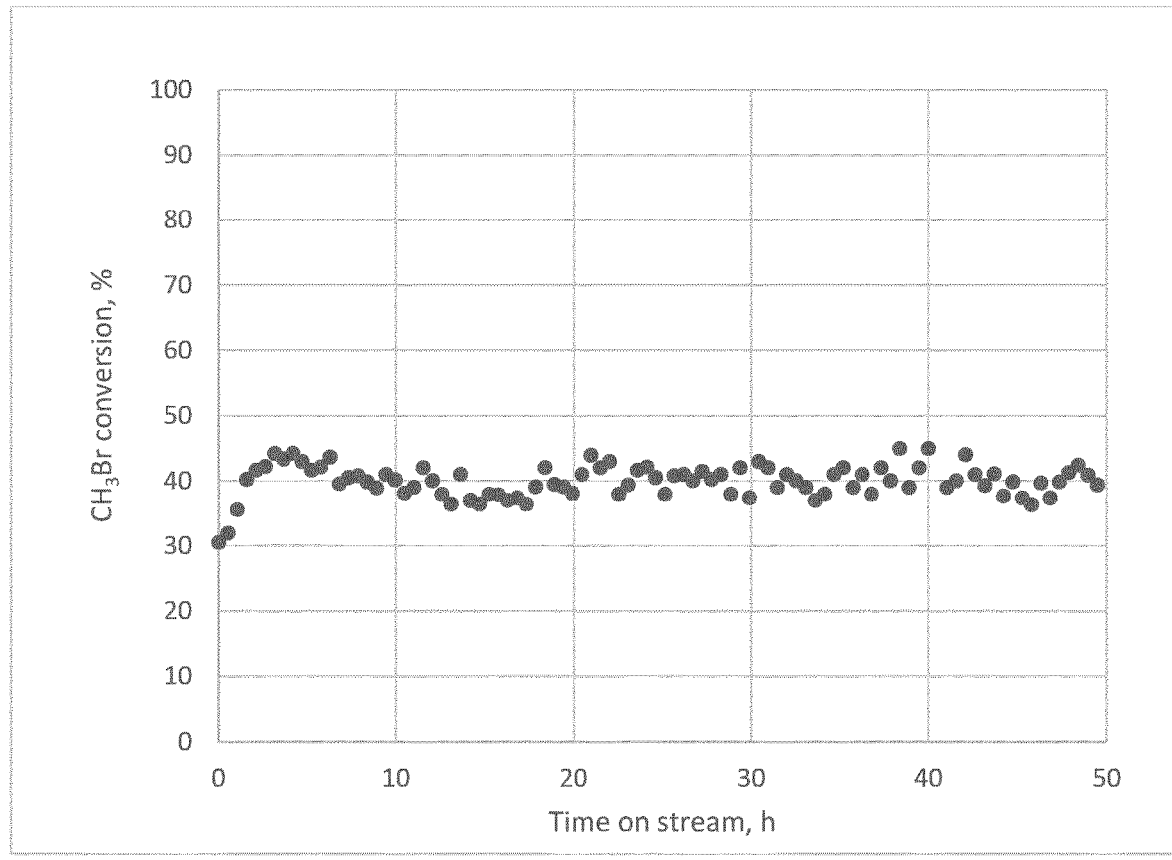
FIG. 7 shows the conversion trend of methyl bromide thanks to the catalyst of the first catalyst composition per the disclosure.

The conversion plot of methyl bromide is reported in FIG. 4 and shows, after a quick increase of the reaction rate during the first hour, a steady conversion comprised between 35% and 45% for at least 10 hours. The experiment was also conducted for a time of 50 hours and no decrease of the conversion has been observed, as shown in FIG. 7.

Example 5

In this example, the catalyst from example 1, namely the silicalite from the MFI family shaped with a SiO$_2$ binder has been used in the cracking step at a temperature of 550° C., with a weight hourly space velocity of 10 h$^{-1}$ and at a pressure of 0.7 MPa.

Table 4 indicates the results of the cracking step according to example 4

TABLE 4

| Conditions and results of the cracking step | |
| --- | --- |
| | Example 4 silicalite# with SiO$_2$ binder |
| Catalyst | |
| SAR† | >200 |
| Temperature (° C.) | 550 |
| Pressure (MPa) | 0.7 |
| WHSV (h$^{-1}$) | 10 |

TABLE 4-continued

| Conditions and results of the cracking step | |
| --- | --- |
| Product | |
| methane | 0.9 |
| ethane | 1.1 |
| C3 | 2.3 |
| C4 | 7.7 |
| C5 | 1.8 |
| C6 paraffins | 1.1 |
| Total selectivity to alkane | 14.9 |
| ethylene | 13.4 |
| propylene | 55.5 |
| C4= | <0.01 |
| C5= | <0.01 |
| C6= | <0.01 |
| Aromatics | 6.5 |
| Bromides | 0.3 |
| Conversion | >99 |
| Yield of ethylene and propylene | >62 |

†as defined from TPD measurement.

Using the process of the present disclosure, it was thus possible to obtain a yield of ethylene and propylene from methyl bromide as starting material of at least 62%.

The invention claimed is:

1. Process for converting one or more alkyl halides to ethylene and propylene, said process comprising the following steps:
    a) providing a feedstream comprising one or more alkyl halides; optionally, diluted in at least one diluent;
    b) providing a first catalyst composition and a second catalyst composition, said second catalyst composition comprising a cracking catalyst;
    c) contacting said feedstream with said first catalyst composition in a first reaction zone under first reaction conditions to provide a first product stream; and
    d) subjecting at least a part of said first product stream to an Olefin Catalytic Cracking with said second catalyst composition in a second reaction zone under second reaction conditions to provide a second product stream,
the process is characterized in that it further comprises a step of steaming said first catalyst composition before the step (c), and in that said first catalyst composition comprises one or more zeolites and a binder, wherein said one or more zeolites comprise at least one 10-membered ring channel.

2. The process according to claim 1, characterized in that said step of steaming is followed by an extraction step.

3. The process according to claim 1, characterized in that the one or more zeolites in the first catalyst composition are selected from the group of MFI, MEL, FER, MTT, MWW, TON, EUO and MRE families, said one or more zeolites having a Si/Al molar ratio in the framework of the zeolite of at least 10 as determined by TPD before the step of steaming.

4. The process according to claim 1, characterized in that said binder in said first catalyst composition is selected from silica, clays, calcium phosphates, magnesium phosphates and mullite.

5. The process according to claim 1, characterized in that said binder in said first catalyst composition is present in an amount of at least 10 wt. % as based on the total weight of the first catalyst composition, preferably of at least 40 wt. %.

6. The process according to claim 1, characterized in that said one or more zeolites in the first catalyst composition have Bronsted acid sites in a concentration inferior to 100 µmol/g-cat as determined by $NH_3$-Temperature Programmed Desorption.

7. The process according to claim 1, characterized in that said first catalyst composition further comprises at least 0.1 wt. % of phosphorous based on the total weight of the first catalyst composition.

8. The process according to claim 1, characterized in that said first catalyst composition further comprises phosphoric acid and magnesium nitrate.

9. The process according to claim 1, characterized in that said first catalyst composition is blended with at least one metal-containing material.

10. The process according to claim 9, characterized in that the at least one metal-containing material is an alkaline earth metal-containing material which comprises at least one alkaline earth metal is selected from beryllium, magnesium, calcium, strontium, barium and any mixtures thereof.

11. The process according to claim 9, characterized in that the at least one metal-containing material has an anion selected from the group of oxides, silicates, aluminates, titanates, phosphates, borates and borosilicates.

12. The process according to claim 1, characterized in that said one or more zeolites of the first catalyst composition contain less than 1000 wt. ppm of alkali metals as determined by XRF based on the total weight one or more zeolites of the first catalyst composition.

13. The process according to claim 1, characterized in that said one or more zeolites of the first catalyst composition contain less than 5000 wt. ppm of transition metals as determined by XRF as based on the total weight one or more zeolites of the first catalyst composition.

14. The process according to claim 1, characterized in that said cracking catalyst comprises one or more zeolites and/or one or more clays.

15. The process according to claim 14, characterized in that said cracking catalyst comprises one or more zeolites selected from silicalites from the MFI family, crystalline silicate from the MFI family with a Si/Al atomic ratio of at least 180, crystalline silicate from the MEL family with a Si/Al atomic ratio ranging between 150 and 800, and/or phosphorous-modified zeolite from the MFI, MEL, FER, or MOR family.

16. The process according to claim 1, characterized in that the second reaction conditions of step (d) include a reaction temperature ranging from 500° C. to 600° C.

17. The process according to claim 1, characterized in that the second reaction conditions of step (d) include a weight hourly space velocity comprised between 0.1 $h^{-1}$ and 100 $h^{-1}$.

18. The process according to claim 1, characterized in that step (c) further comprises separating from the first product stream a C4+ stream and the step (d) comprises subjecting said C4+ stream to an Olefin Catalytic Cracking with said second catalyst composition in a second reaction zone under second reaction conditions to provide a second product stream.

19. The process according to claim 1, characterized in that said step (d) of contacting said first product stream with said second catalyst composition is followed by a step (e) of performing a separation of ethylene and propylene from said second product stream.

20. The process according to claim 1, characterized in that said process further comprises one or more of the following sub-steps:
   i. removing hydrogen halide from said first product stream before the step (d) or from said second product stream after the step (d);
   ii. recovering at least a part of the unreacted one or more alkyl halides before or after the step (d), followed by a step of reinjecting said at least a part of unreacted one or more alkyl halides into the feedstream of step (a);
   iii. removing aromatics from said first product stream before the step (d) or from said second product stream after the step (d).

* * * * *